(12) United States Patent
Jordan et al.

(10) Patent No.: US 8,679,839 B2
(45) Date of Patent: Mar. 25, 2014

(54) CELL LINE FROM ROUSETTUS AS HOST CELL FOR PATHOGEN AMPLIFICATION

(75) Inventors: Ingo Jordan, Berlin (DE); Deborah Horn, Berlin (DE); Volker Sandig, Berlin (DE)

(73) Assignee: Probiogen AG, Berlin (DE)

( * ) Notice: Subject to any disclaimer, the term of this patent is extended or adjusted under 35 U.S.C. 154(b) by 119 days.

(21) Appl. No.: 12/921,142

(22) PCT Filed: Mar. 4, 2009

(86) PCT No.: PCT/EP2009/001540
§ 371 (c)(1),
(2), (4) Date: Dec. 6, 2010

(87) PCT Pub. No.: WO2009/109377
PCT Pub. Date: Sep. 11, 2009

(65) Prior Publication Data
US 2011/0269116 A1    Nov. 3, 2011

(30) Foreign Application Priority Data

Mar. 4, 2008 (EP) .................................. 08102277
Jul. 23, 2008 (EP) .................................. 08161013

(51) Int. Cl.
*C12N 5/10* (2006.01)
*A01N 63/00* (2006.01)
*C12N 5/02* (2006.01)

(52) U.S. Cl.
USPC ........ 435/363; 424/93.21; 424/93.7; 435/325

(58) Field of Classification Search
USPC .................... 435/363, 325; 424/93.21, 93.7
See application file for complete search history.

(56) References Cited

U.S. PATENT DOCUMENTS

| | | | |
|---|---|---|---|
| 5,665,589 A * | 9/1997 | Harris et al. .................. | 435/370 |
| 7,192,759 B1 * | 3/2007 | Pau et al. ..................... | 435/235.1 |
| 7,771,993 B2 * | 8/2010 | Stedman et al. ............. | 435/320.1 |
| 2008/0227146 A1 * | 9/2008 | Sandig et al. ................ | 435/69.1 |

FOREIGN PATENT DOCUMENTS

| | | | |
|---|---|---|---|
| DD | 294 039 | * | 9/1991 |
| EP | 1939281 A1 | * | 7/2008 |
| WO | 2005/042728 A | | 5/2005 |
| WO | 2007/054516 A | | 5/2007 |

OTHER PUBLICATIONS

Towner et al Marburg virus infection detected in a common African bat JS Towner, . . .—PLoS One, 2007 pp. 1-4.*
Hang et al., Journal of Virological Methods 109 (2003) 125__/131 Establishment of a GFP-based indicator cell line to quantitate feline foamy virus.*
Omatsu et al., Biological characters of bats in relation to natural reservoir of emerging viruses, Comparative Immunology, Microbiol. and Infectious Diseases, Sep. 1, 2007; 30(5-6):357-374.
Patrascu, Bovine leukemia virus. VII. In vitro replication of virus in bat lung cell culture NBL BLV 2, Revue Roumaine de Medecine, Virologie, Jul. 1, 1988; 39(3):199-205.
Drexler et al., Highly attenuated modified *Vaccinia virus* Ankara replicates in baby hamster kidney cells, a potential host for virus propagation, but not in various human transformed and primary cells, J. of General Virology, Feb. 1, 1998; 79 (2):347-352.
Rourou et al., A microcarrier cell culture process for propagating rabies virus in Vero cells grown in a stirred bioreactor under fully anima component free conditions, Vaccine, Apr. 19, 2007; 25(19):3879-3889.
Genzel et al., Serum-free influenza virus production avoiding washing steps and medium exchange in large-scale microcarrier culture, Vaccine, Apr. 12, 2006; 24(16):3621-3272.
Jordan et al., An avian cell line designed for production of highly attenuated viruses, Vaccine, Jan. 5, 2009; 27 (5):748-756.

* cited by examiner

*Primary Examiner* — Maria Leavitt
(74) *Attorney, Agent, or Firm* — McDonnell Boehnen Hulbert & Berghoff LLP

(57) ABSTRACT

The present invention relates to permanent cell lines from chiropterans suitable for amplification and production of microbial agents, preferably viruses, and its use for diagnostic or therapeutic purposes.

Figure 1:
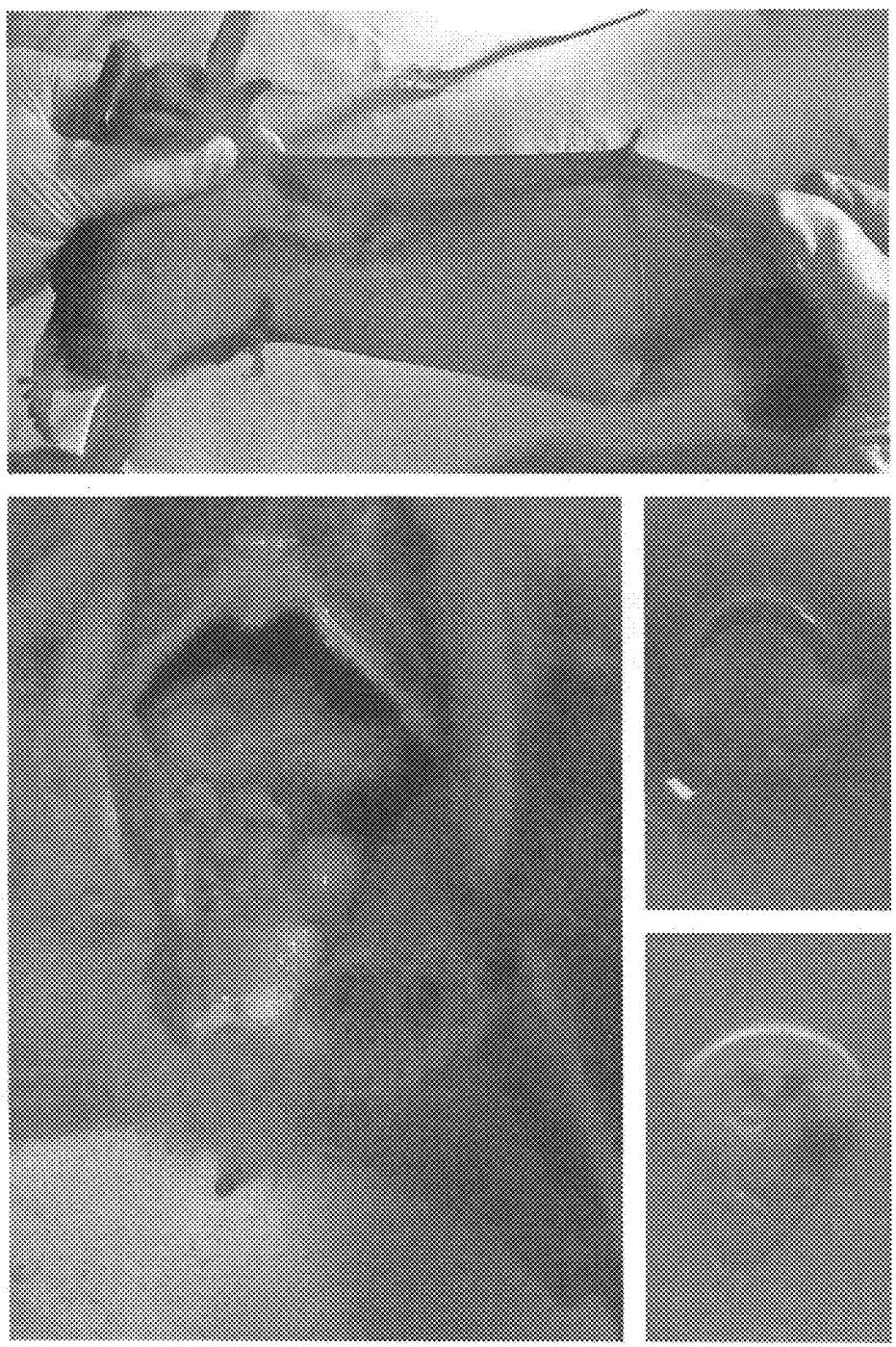

17 Claims, 14 Drawing Sheets
(12 of 14 Drawing Sheet(s) Filed in Color)

SEQUENCE LISTING

```
<160> NUMBER OF SEQ ID NOS: 7

<210> SEQ ID NO 1
<211> LENGTH: 8681
<212> TYPE: DNA
<213> ORGANISM: Artificial
<220> FEATURE:
<223> OTHER INFORMATION: transfection vector # G56

<400> SEQUENCE: 1
cttccgcttc ctcgctcact gactcgctgc gctcggtcgt tcggctgcgg cgagcggtat      60
cagctcactc aaaggcggta atacggttat ccacagaatc agggggataac gcaggaaaga    120 acatgtgagc aaaaggccag caaaagccca ggaaccgtaa aaaggccgcg ttgctggcgt    180
ttttccatag gctccgcccc cctgacgagc atcacaaaaa tcgacgctca agtcagaggt    240
ggcgaaaccc gacaggacta taaagatacc aggcgtttcc ccctggaagc tccctcgtgc    300
gctctcctgt tccgaccctg ccgcttaccg gatacctgtc cgcctttctc ccttcgggaa    360
gcgtggcgct ttctcatagc tcacgctgta ggtatctcag ttcggtgtag gtcgttcgct    420
ccaagctggg ctgtgtgcac gaacccccg ttcagcccga ccgctgcgcc ttatccggta    480
actatcgtct tgagtccaac ccggtaagac acgacttatc gccactggca gcagccactg    540
gtaacaggat tagcagagcg aggtatgtag gcggtgctac agagttcttg aagtggtggc    600
ctaactacgg ctacactaga aggacagtat ttggtatctg cgctctgctg aagccagtta    660
ccttcggaaa aagagttggt agctcttgat ccggcaaaca aaccaccgct ggtagcggtg    720
gtttttttgt ttgcaagcag cagattacgc gcagaaaaaa aggatctcaa gaagatcctt    780
tgatcttttc tacggggtct gacgctcagt ggaacgaaaa ctcacgttaa gggattttgg    840
tcatgagatt atcaaaaagg atcttcacct agatcctttt aaattaaaaa tgaagtttta    900
aatcaatcta agtatatatg agtaaacttg gtctgacaga ttaccaatgc ttaatcagtg    960
aggcacctat ctcagcgatc tgtctatttc gttcatccat agttgcctga ctccccgtcg   1020
tgtagataac tacgatacgg gagggcttac catctggccc cagtgctgca atgataccgc   1080
gagacccacg ctcaccggct ccagatttat cagcaataaa ccagccagcc ggaagggccg   1140
agcgcagaag tggtcctgca actttatccg cctccatcca gtctattaat tgttgccggg   1200
aagctagagt aagtagttcg ccagttaata gtttgcgcaa cgttgttgcc attgctacag   1260
gcatcgtggt gtcacgctcg tcgtttggta tggcttcatt cagctccggt tcccaacgat   1320
caaggcgagt tacatgatcc cccatgttgt gcaaaaaagc ggttagctcc ttcggtcctc   1380
cgatcgttgt cagaagtaag ttggccgcag tgttatcact catggttatg gcagcactgc   1440
ataattctct tactgtcatg ccatccgtaa gatgcttttc tgtgactggt gagtactcaa   1500
ccaagtcatt ctgagaatag tgtatgcggc gaccgagttg ctcttgcccg gcgtcaatac   1560
gggataatac cgcgccacat agcagaactt taaaagtgct catcattgga aaacgttctt   1620
```

-continued

```
cggggcgaaa actctcaagg atcttaccgc tgttgagatc cagttcgatg taacccactc    1680
gtgcacccaa ctgatcttca gcatctttta cttttcaccag cgtttctggg tgagcaaaaa   1740
caggaaggca aaatgccgca aaaagggaa taagggcgac acggaaatgt tgaatactca    1800
tactcttcct ttttcaatat tattgaagca tttatcaggg ttattgtctc atgagcggat    1860
acatatttga atgtatttag aaaaataaac aaatagggg tccgcgcaca tttccccgaa     1920
aagtgccacc tgtatgcggt gtgaaatacc gcacagatgc gtaaggagaa ataccgcat    1980 caggaaattg taagcgttaa taattcagaa gaactcgtca agaaggcgat agaaggcgat   2040
gcgctgcgaa tcgggagcgg cgataccgta agcacgagg aagcggtcag cccattcgcc    2100
gccaagctct tcagcaatat cacgggtagc caacgctatg tcctgatagc ggtccgccac   2160
acccagccgg ccacagtcga tgaatccaga aaagcggcca ttttccacca tgatattcgg   2220
caagcaggca tcgccatggg tcacgacgag atcctcgccg tcgggcatgc tcgccttgag   2280
cctggcgaac agttcggctg gcgcgagccc ctgatgctct tcgtccagat catcctgatc   2340
gacaagaccg gcttccatcc gagtacgtgc tcgctcgatg cgatgtttcg cttggtggtc   2400
gaatgggcag gtagccggat caagcgtatg cagccgccgc attgcatcag ccatgatgga   2460
tactttctcg gcaggagcaa ggtgagatga caggagatcc tgccccggca cttcgcccaa   2520
tagcagccag tcccttcccg cttcagtgac aacgtcgagc acagctgcgc aaggaacgcc   2580
cgtcgtggcc agccacgata gccgcgctgc ctcgtcttgc agttcattca gggcaccgga   2640
caggtcggtc ttgacaaaaa gaaccgggcg cccctgcgct gacagccgga acacggcggc   2700
atcagagcag ccgattgtct gttgtgccca gtcatagccg aatagcctct ccacccaagc   2760
ggccggagaa cctgcgtgca atccatcttg ttcaatcatg cgaaacgatc ctcatcctgt   2820
ctcttgatca gagcttgatc ccctgcgcca tcagatcctt ggcggcgaga aagccatcca   2880
gtttactttg cagggcttcc caaccttacc agagggcgcc ccagctggca attccggttc   2940
gcttgctgtc cataaaaccg cccagtctag ctatcgccat gtaagcccac tgcaagctac   3000
ctgctttctc tttgcgcttg cgttttccct tgtccagata gcccagtagc tgacattcat   3060
ccggggtcag caccgtttct gcggactggc ttttctacgtg aaaaggatct aggtgaagat   3120
cctttttgat aatctcatgc ctgacattta tattccccag aacatcaggt taatggcgtt   3180
tttgatgtca ttttcgcggt ggctgagatc agccacttct tccccgataa cggagaccgg   3240
cacactggcc atatcggtgg tcatcatgcg ccagctttca tccccgatat gcaccaccgg   3300
gtaaagttca cgggagactt tatctgacag cagacgtgca ctggccaggg ggatcaccat   3360
ccgtcgcccc ggcgtgtcaa taatatcact ctgtacatcc acaaacagac gataacggct   3420
ctctctttta taggtgtaaa ccttaaactg ccgtaccatg ttcttttcctg cgttatcccc   3480 tgattctgtg gataaccgta ttaccgccat gcattagtta ttaatggttg gggttgcgcc   3540
ttttccaagg cagccctggg tttgcgcagg acgcggctg ctctgggcgt ggttccggga    3600
aacgcagcgg cgccgaccct gggtctcgca cattcttcac gtccgttcgc agcgtcaccc   3660
ggatcttcgc cgctacccct tgtgggcccc cggcgacgct tcctcgtccg cccctaagtc   3720
gggaaggttc cttgcggttc gcggcgtgcc ggacgtgaca aacggaagcc gcacgtctca   3780 ctagtacccct cgcagacgga cagcgccagg gagcaatggc agcgcgccga ccgcgatggg   3840
ctgtggccaa tagcggctgc tcagcagggc gcgccgagag cagcggccgg gaaggggcgg   3900
tgcgggaggc ggggtgtggg gcggtagtgt gggccctgtt cctgcccgcg cggtgttccg   3960
cattctgcaa gcctccggag cgcacgtcgg cagtcggctc cctcgttctc gagttatagt   4020
```

```
cagctgacgt gtagtgtatt tatacccggt gagttcctca agaggccact cttgagtgcc    4080
agcgagtaga gttttctcct ccgagccgct ccgacaccgg gactgaaaat gagacatatt    4140
atctgccacg gaggtgttat taccgaagaa atggccgcca gtcttttgga ccagctgatc    4200
gaagaggtac tggctgataa tcttccacct cctagccatt ttgaaccacc taccctttcac   4260
gaactgtatg atttagacgt gacggccccc gaagatccca acgaggaggc ggtttcgcag    4320
attttttccg actctgtaat gttggcggtg caggaaggga ttgacttact cacttttccg    4380
ccggcgcccg gttctccgga gccgcctcac cttttcccggc agcccgagca gccggagcag   4440
agagccttgg gtccggtttc tatgccaaac cttgtaccgg aggtgatcga tcttacctgc    4500
cacgaggctg gctttccacc cagtgacgac gaggatgaag agggtgagga gtttgtgtta    4560
gattatgtgg agcaccccgg gcacggttgc aggtcttgtc attatcaccg gaggaatacg    4620
ggggacccag atattatgtg ttcgctttgc tatatgagga cctgtggcat gtttgtctac    4680
agtaagtgaa aattatgggc agtgggtgat agagtggtgg gtttggtgtg gtaattttttt   4740
ttttaattt tacagttttg tggtttaaag aattttgtat tgtgattttt ttaaaaggtc     4800
ctgtgtctga acctgagcct gagcccgagc cagaaccgga gcctgcaaga cctacccgcc    4860
gtcctaaaat ggcgcctgct atcctgagac gcccgacatc acctgtgtct agagaatgca    4920
atagtagtac ggatagctgt gactccggtc cttctaacac acctcctgag atacacccgg    4980
tggtcccgct gtgccccatt aaaccagttg ccgtgagagt tggtgggcgt cgccaggctg    5040
tggaatgtat cgaggacttg cttaacgagc ctgggcaacc tttggacttg agctgtaaac    5100
gccccaggcc ataaggtgta aacctgtgat tgcgtgtgtg gttaacgcct ttgtttgctg    5160
aatgagttga tgtaagttta ataaagggtg agataatgtt taacttgcat ggcgtgttaa    5220
atggggcggg gcttaaaggg tatataatgc gccgtgggct aatcttggtt acgaattcgt    5280
ttctagtgga tccaaatgag tcttcggacc tcgcggggc cgcttaagcg gtggttaggg     5340
tttgtctgac gcgggggggag ggggaaggaa cgaaacactc tcattcggag gcggctcggg   5400
gtttggtctt ggtggccacg ggcacgcaga agagcgccgc gatcctctta agcacccccc    5460
cgccctccgt ggaggtgggg gtttggtcgg cgggtggtaa ctggcgggcc gctgactcgg    5520
gcgggtcgcg cgccccagag tgtgaccttt tcggtctgct cgcagacccc cgggcggcgc    5580
cgccgcggcg cgacgggct cgctgggtcc taggctcaat ggggaccgta tacgtggaca     5640
ggctctggag catccgcacg actgcggtga tattaccgga gaccttctgc gggacgagcc    5700
gggtcacgcg gctgacgcgg agcgtccgtt gggcgacaaa caccaggacg gggcacaggt    5760
acactatctt gtcacccgga ggcgcgaggg actgcaggag cttcagggag tggcgcagct    5820
gcttcatccc cgtggcccgt tgctcgcgtt tgctggcggt gtccccggaa gaaatatatt    5880
tgcatgtctt tagttctatg atgacacaaa ccccgcccag cgtcttgtca ttggcgaatt    5940
cgaacacgca gatgcagtcg gggcggcgcg gtcccaggtc cacttcgcat attaaggtga    6000
cgcgtgtggc ctcgaatacc gagcgaccct gcagcgaccc gcttaacagc gtcaacagcg    6060
tgccgcagat cgctaccgga ctcagatccc ctacctgcgc ctctcttccc cagacctgcg    6120
cgctactgcg gctcgggcgg tcgctcgcct ggctctgctc catttgactg tctgtgtgca    6180
gtcgcagaac ttcgaagagg gttttgcgct ccatccgtgg cgtttcgctt ttgttcggtt    6240
ttgttgttta tttcattttt tttttccgga gagaggcgag gcggtggtcc acacccgccc    6300
gaggaggaag gatctcgagc atggaggctt gggagtgttt ggaagatttt tctgctgtgc    6360
gtaacttgct ggaacagagc tctaacagta cctcttggtt ttggaggttt ctgtggggct    6420
```

```
catcccaggc aaagttagtc tgcagaatta aggaggatta caagtgggaa tttgaagagc    6480
ttttgaaatc ctgtggtgag ctgtttgatt ctttgaatct gggtcaccag gcgcttttcc    6540
aagagaaggt catcaagact ttggattttt ccacaccggg gcgcgctgcg gctgctgttg    6600
cttttttgag ttttataaag gataaatgga gcgaagaaac ccatctgagc gggggtacc     6660 tgctggattt tctggccatg catctgtgga gagcggttgt gagacacaag aatcgcctgc    6720
tactgttgtc ttccgtccgc ccggcgataa taccgacgga ggagcagcag cagcagcagg    6780
aggaagccag gcggcggcgg caggagcaga gcccatggaa cccgagagcc ggcctggacc    6840
ctcgggaatg aatgttgtac aggtggctga actgtatcca gaactgagac gcattttgac    6900
aattacagag gatgggcagg ggctaaaggg ggtaaagagg gagcggggg cttgtgaggc     6960 tacagaggag gctaggaatc tagcttttag cttaatgacc agacaccgtc ctgagtgtat    7020
tacttttcaa cagatcaagg ataattgcgc taatgagctt gatctgctgg cgcagaagta    7080
ttccatagag cagctgacca cttactggct gcagccaggg gatgattttg aggaggctat    7140
tagggtatat gcaaaggtgg cactaggcc agattgcaag tacaagatca gcaaacttgt     7200
aaatatcagg aattgttgct acatttctgg gaacggggcc gaggtggaga tagatacgga    7260
ggatagggtg gcctttagat gtagcatgat aaatatgtgg ccggggtgc ttggcatgga     7320 cggggtggtt attatgaatg taaggtttac tggccccaat tttagcggta cggttttcct    7380
ggccaatacc aaccttatcc tacacggtgt aagcttctat gggtttaaca atacctgtgt    7440
ggaagcctgg accgatgtaa gggttcgggg ctgtgccttt tactgctgct ggaagggggt    7500
ggtgtgtcgc cccaaaagca gggcttcaat taagaaatgc ctcttgaaa ggtgtacctt     7560 gggtatcctg tctgagggta actccagggt gcgccacaat gtggcctccg actgtggttg    7620
cttcatgcta gtgaaaagcg tggctgtgat taagcataac atggtatgtg caactgcga    7680 ggacagggcc tctcagatgc tgacctgctc ggacggcaac tgtcacctgc tgaagaccat    7740
tcacgtagcc agccactctc gcaaggcctg gccagtgttt gagcataaca tactgacccg    7800
ctgttccttg catttgggta acaggagggg ggtgttccta ccttaccaat gcaatttgag    7860
tcacactaag atattgcttg agcccgagag catgtccaag gtgaacctga acggggtgtt    7920
tgacatgacc atgaagatct ggaaggtgct gaggtacgat gagacccgca ccaggtgcag    7980
accctgcgag tgtggcggta acatattag gaaccagcct gtgatgctgg atgtgaccga    8040
ggagctgagg cccgatcact tggtgctggc ctgcacccgc gctgagtttg gctctagcga    8100
tgaagataca gattgaggat aacacggaag gagacaatac cggaaggaac ccgcgctatg    8160
acggcaataa aaagacagaa taaaacgcac ggtgttgggt cgtttgttca taaacgcggg    8220
gttcggtccc agggctggca ctctgtcgat accccaccga gacccccattg gggccaatac   8280 gcccgcgttt cttccttttc cccaccccac cccccaagtt cgggtgaagg cccagggctc    8340
gcagccaacg tcggggcggc agcttaagat taagggcgaa ttcgtttaaa cctgcaggac    8400
tagaaacctg caggactagt ccctttagtg agggttaatt ctgagcttgg cgtaatcatg    8460
gtcatagctg tttcctgtgt gaaattgtta tccgctcaca attccacaca acatacgagc    8520
cggaagcata aagtgtaaag cctggggtgc ctaatgagtg agctaactca cattaattgc    8580
gttgcgctca ctgcccgctt tccagtcggg aaacctgtcg tgccagctgc attaatgaat    8640
cggccaacgc gcggggagag gcggtttgcg tattgggcgc t                        8681

<210> SEQ ID NO 2
<211> LENGTH: 24
<212> TYPE: DNA
```

```
-continued

<213> ORGANISM: Artificial
<220> FEATURE:
<223> OTHER INFORMATION: primer

<400> SEQUENCE: 2
actcgagctg acgtgtagtg tatt                                          24

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
cacacgcaat cacaggtt                                                 18

<210> SEQ ID NO 4
<211> LENGTH: 25
<212> TYPE: DNA
<213> ORGANISM: Artificial
<220> FEATURE:
<223> OTHER INFORMATION: primer

<400> SEQUENCE: 4
actcgagtca tggaggcttg ggagt                                         25

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
acacatttca gtacctca                                                 18

<210> SEQ ID NO 6
<211> LENGTH: 26
<212> TYPE: DNA
<213> ORGANISM: Artificial
<220> FEATURE:
<223> OTHER INFORMATION: primer

<400> SEQUENCE: 6
gagattaatg gttggggttg cgcctt                                        26

<210> SEQ ID NO 7
<211> LENGTH: 27
<212> TYPE: DNA
<213> ORGANISM: Artificial
<220> FEATURE:
<223> OTHER INFORMATION: primer

<400> SEQUENCE: 7
aactcgagaa cgagggagcc gactgcc                                       27
```

CELL LINE FROM ROUSETTUS AS HOST CELL FOR PATHOGEN AMPLIFICATION

The present invention relates to permanent cell lines from chiropterans suitable for amplification and production of microbial agents, preferably viruses, and its use for diagnostic or therapeutic purposes.

BACKGROUND OF THE INVENTION

Within the mammalia bats are second only to rodents in species diversity. The taxonomic order of bats is Chiroptera, further classified into the suborders Megachiroptera and Microchiroptera, usually referred to as fruit bats or megabats and insectivorous bats or microbats, respectively. The Megachiroptera contains a single family, the Pteropodidae, whereas the Microchiroptera are subdivided into seven superfamilies comprising a total of seventeen families.

Greater taxonomic complexity of microbats is mirrored in their worldwide geographic distribution that includes temperate climate zones and the Americas compared to megabats that are confined to tropical and subtropical regions of the Eastern Hemissphere.

Microbats have tails and one clawed finger on each wing, megabats generally have no tail and two clawed fingers on each wing. Megabats have simple ears with the rim of the pinnae forming a closed ring and simple snouts without the complicated nose leaves supporting production of echolocation signals. Microbats are insectivorous, hunt small animals or feed on blood. Megabats are frugivorous or nectarivorous.

Microbats but not megabats are able to perform echolocation for orientation and to avoid obstacles. Megabats rely on their acute sense of vision; indeed, only in megabats (but not in microbats) neuronal organisation connecting retina and midbrain appears just as advanced as it is in primates (Pettigrew 1986 in Science 231, 1304-1306). As the single exception within the megabats *Rousettus aegyptiacus* is also capable of sonar orientation. However, the echolocation system of *Rousettus* is not related to the sophisticated laryngeal echolocation of the microbats (Springer 2001 et al. in Proc. Natl. Acad. Sci. U.S.A. 96, 6241-6246; Holland et al. 2004 in J. Exp. Biol. 207, 4361-4369). It is the result of convergent evolution and comparatively simple where the emitted signal is produced as low-energy clicks by the tongue. Furthermore, *Rousettus* ears lack the muscles and innervation required for self-deafening to improve information content of the reflected sound.

The profound differences between microbats and megabats in geographical distribution, behaviour, anatomy and physiology stimulated a controversial discussion whether the flying mammals truly are monophyletic. Tree building based on mitochondrial (Lin and Penny 2001 in Mol. Biol. Evol. 18, 684-688), genomic sequences incorporating the scarce available fossil data (Springer et al. 2001; Teeling et al. 2005 in Science 307, 580-584) and supertree algorithm (Emonds et al. 2007 in Nature 446, 507-512) suggests that bats have evolved from a common ancestor with megabats in a distinct clade. Fossilation of the most primitive bat found to date (a bat already capable of flight but not yet of echolocation, still with claws on all digits) is dated to have occurred 52.5 million years ago (Simmons et al. 2008 in Nature 451, 818-822). Powerful larnygal echolocation has evolved subsequently only once but was lost in the megabats where it was reinvented in its simple form only by *Rousettus*.

Bats are vectors and reservoir for a number of important and emerging viruses, including members of the filoviridae (such as Marburg and Ebola virus), paramyxoviridae (such as Nipah virus), rhabdoviridae (such as rabies and European bat lyssavirus) and coronaviridae (the SARS-CoV).

Most surprising is the fact that bats appear not or only minimally to be affected by a variety of pathogens that usually are fatal to vertebrates.

For example, Ebola virus was detected in wild megabats collected at sites near to infected gorilla and chimpanzee carcasses. The megabats were positive for genomic RNA sequences from or antibodies against Ebola but did not display any disease symptoms (Leroy et al. 2005 in Nature 438, 575-576). Transfer of virus probably occurs via fruit contaminated by the megabats during foraging.

Nipah and Hendra viruses are associated with high mortality but, again, in megabats that serve as reservoirs there are no symptoms (Reynes et al. 2005 in Emerg. Inf. Diseases 11, 1042-1047). Microbats appear not to carry Nipah or Hendrah viruses.

According to the World Health Organisation, 55000 human deaths from rabies are reported annually. Rabies is invariably fatal to mammals with extremely rare and unusual exceptions: in spotted hyenas of the Serengeti a special, possibly attenuated strain of rabies has established endemic persistence (East et al. 2001 in Proc. Natl. Acad. Sci. U.S.A. 98, 15026-15031), and a single wild oncilla with antibody titers suggestive of exposure to rabies virus but otherwise clinically inapparent was captured in Bolivia (Deem et al. 2004 in J. Wildlife Diseases 40, 811-815). Certain bat species, however, frequently are found to carry rabies virus without overt symptoms (for example Poel et al. 2005 in Emerging Inf. Dis. 11, 1854-1859 for European bats and Messenger et al. 2002 in Clinical Inf. Dis. 35, 738-747). Rabies ecology is complicated and many wild and domestic animals are vectors depending on country and geographic region. In Latin America main vectors and reservoirs for rabies appear to be hemovorous (vampire) bats and dogs (Ito et al. 2001 in Virology 284, 214-222). Insectivorous bats are important vectors for cryptic rabies in developed countries: transmission of virus after encounter with a bat has not been realized until it is too late for post-exposure prophylaxis (Feder et al. 1997 in Lancet 350, 1300). Most fascinating and further highlighting significance of bats for rabies dissemination is a phylogenetic analysis suggesting that possibly an insect rhabdovirus transferred into an insectivorous bat, evolved into bat lyssaviruses and from there repeated further host switching into the carnivora has allowed rhabies virus to emerge as it is known in contemporary mammals (Badrane and Tordo 2001 in J. Virol. 75, 8096-8104).

Spread of an agent causing severe acute respiratory syndrome (SARS) in the human population nearly created a pandemic in 2002/2003. With rapid identification of the pathogen, a coronavirus named SARS-CoV, it was subsequently realized that SARS-CoV entered the human populatian via a zoonotic event at a Chinese meat market with civet cats as source (Guan et al. 2003 in Science 302, 276-278). Recent analysis indicate that fruit bats and microbats are reservoir for SARS-CoV (Li et al. 2005 in Science 310, 676-679); again, infection may have initiated via spill-over to other species after a pathogen evolved in bats where it does not cause disease.

The fatal suitability of bats as vectors may be due to a coincidental combination of behavioural, evolutionary and physiological properties:

Many bats tend to live in large communities at high population density thus facilitating repeated exposure, spread and maintenance of certain pathogens. Spread within a roost may be further enhanced or modulated if the act of echolocation generates an aerosol of pathogens suspended in saliva and mucus from mouth or nose of the animals. Transmission with aerolized pathogens may cause infection with low viral loads or unusual entry into the recipient (for example, mucosal infection with rabies or flavivirus rather than parenteral via bite or insect vector) and this may lead to persistent and subclinical infection.

Bats can fly and thus a carrier of a disease may cover large areas or gain more easily access to human shelters to transmit a pathogen. This propability for transmission is further increased by the long lifespan of bats.

Self-powered flight places a large burden on efficient metabolism. To conserve energy, some bats hybernate or reduce body temperature even for daily sleep. The adaptation to high metabolic rates, hypothermia by itself and possibly intermittent depression of the innate and adaptive immune system due to these adaptations may help viruses to establish subclinical persistence.

Finally, bats are an evolutionary very old order of the mammalia class. Difficult and enigmatic to trace via fossil and molecular records, the latest common origin of the various bat species has been estimated to have lived 89 million years ago in the late Cretaceous period (Bininda-Emonds et al. 2007 in Nature 446, 507-512). Major speciation of bats appears to have started within the K-T boundary (Teeling et al. 1995 in Science 307, 580-584), a geological signature assumed to have been caused by a catastrophic event approximately 65 million years ago. The K-T boundary separates sediments from the Cretatious and Tertiary periods and coincides with the extinction of dinosaurs and increase of plant and insect diversity—liberating ecological niches and providing new sources for foraging. Being an evolutionary old clade may translate into two properties with respect to suitability as disease vectors: their adaptive immune system may react to certain pathogens very differently compared to the immune system of most mammalia, and some of the more dangerous zoonotic agents may have decreased pathogenicity towards bats due to co-evolution with the flying mammals as reservoir.

In summary, bats are fascinating animals with significant impact on the infectious disease ecology, both as reservoir and vector. Shadowed by the huge taxonomic diversity of microbats, megabats form a unique clade within these unique mammals. Specifically megabats have been implicated as disease carriers for important pathogens such as filoviridae.

Many macroscopic determinants for suitability of bats as vectors have been discussed above. The individual cell also has been shaped by these circumstances. For example, energy expenditure of self-powered flight is high and physiology and biochemistry has to adapt to the increased metabolic requirement. It has recently been suggested that this adaptation extends to the individual cell (Organ et al. 2007 in Nature 446, 180-184): the genome of birds and bats is surprisingly small compared to other vertebrates. A small genome translates into a small nucleus and thus into a small cell volume. Diffusion of dissolved gases, nutrients and metabolites is more efficient in small cells.

On the other side of the evolutionary equation, some viruses that are serious threats today may have adapted to bats as reservoirs and thus evolved to find suitable receptors, cellular cofactors for genome replication, viral protein processing and maturation, and virion morphogenesis and egress.

Thus, properties of cell lines derived from bats may be of profound use from an industrial perspective: it is assumed that important infectious agents find a unique environment in bat cells especially from the Megachiroptera with respect to host range, productivity and formation or avoidance of cytopathic effect. An immortalized cell line derived from a Megachiroptera would be extremely beneficial to virus and vaccine research and to production of prophylactic or therapeutic vaccines or viral vectors. Furthermore, an immortalized cell line derived from a Megachiroptera may allow cell based assays for isolation of pathogens yet insufficiently characterized for PCR or serological diagnosis. Furthermore, we propose using bat cells with their naturally high metabolic advantages as industrial producer cells. To utilize and explore these properties one first has to generate such a cell line. With such a cell line, preferably aided by modern proteomics and genomics, it is identify nodes and factors in the biochemical pathways that are instrumental for transfer of bat cell properties to common producer cells for viruses or proteins such as Vero or CHO. It is also possible to identify and characterize properties evolution has shaped in bats with respect to virus susceptibility and degree of or resistance against an infection. These factors, and the properties they confer, are transferred to suitable host cells from other species, avian, insect or human for example, for generation of therapeutic molecules, attenuated or targeted viruses, and viral vectors in therapeutic or prophylactic approaches.

SUMMARY OF THE INVENTION

Thus, an immortalized cell line from the Megachirpteran *Rousettus aegyptiacus* has been provided. The cell lines have been generated by liposomal transfection of E1 genes from human adenovirus serotype 5 but any means of immortalization via cell cycle induction and inhibition of apoptosis, either by direct targeting of the pathways or random events is possible. A representative cell line, AGE1.R06E has been deposited with the DSMZ under the accession number DSM ACC2902.

We also provide data that indicate surprisingly effecient permissivity and replication potential for the highly attenuated modified vaccinia Ankara (MVA) virus.

The invention thus provides (1) a cell line derived from a bat (Chiroptera) cell immortalized by a defined mechanism (i.e., an immortalized bat cell line);

(2) a preferred embodiment of the cell line of (1) above, which is a primary cell of Megachiroptera *Rousettus aegyptiacus* immortalized by an adenoviral E1 gene, preferably carrying nt 3524 to 8361 of SEQ ID NO:1, most preferably is cell line AGE1.R06E deposited under DSM ACC2902;

(3) a method for preparing the cell line as defined in (1) or (2) above, which comprises immortalizing a starting bat cell;

(4) a method for producing a microbial agent on a cell line as defined in (1) or (2) above, which comprises contacting said cell line with (i) the microbial agent, including infection with the microbial agent, cultivating the infected cells, harvesting the cells or the culture supernatant to retrieve the microbial agent; or (ii) with a nucleic acid sequence encoding said microbial agent, including transfection or transduction with an expression plasmid or in vitro transcribed RNA, cultivating the transfected cells, harvesting the cells or the culture supernatant to retrieve the microbial agent;

(5) a method for diagnosis, identification, retrieval or rescue of a microbial agent which includes exposing the cells from a cell line as defined in (1) or (2) above to medium or biological samples suspected to contain a certain microbial agent; and (6) the use of a cell line as defined in (1) or (2) above for production, diagnosis, identification, retrieval or rescue of a microbial agent (all of the above especially preferred in media free of animal-derived components, either on microcarriers or in true suspension), or for identification of at least one factor important for replication of or resistance against a microbial agent, and application or exogenous expression of this factor or these factors in a cell that is not isolated from a chiropteran.

SHORT DESCRIPTION OF THE FIGURES

The patent or application file contains at least one drawing executed in color. Copies of this patent or patent application publication with color drawing(s) will be provided by the Office upon request and payment of the necessary fee.

FIG. 1: Isolation of cells from a fetus of *Rousettus aegyptiacus*.

Figure 2:
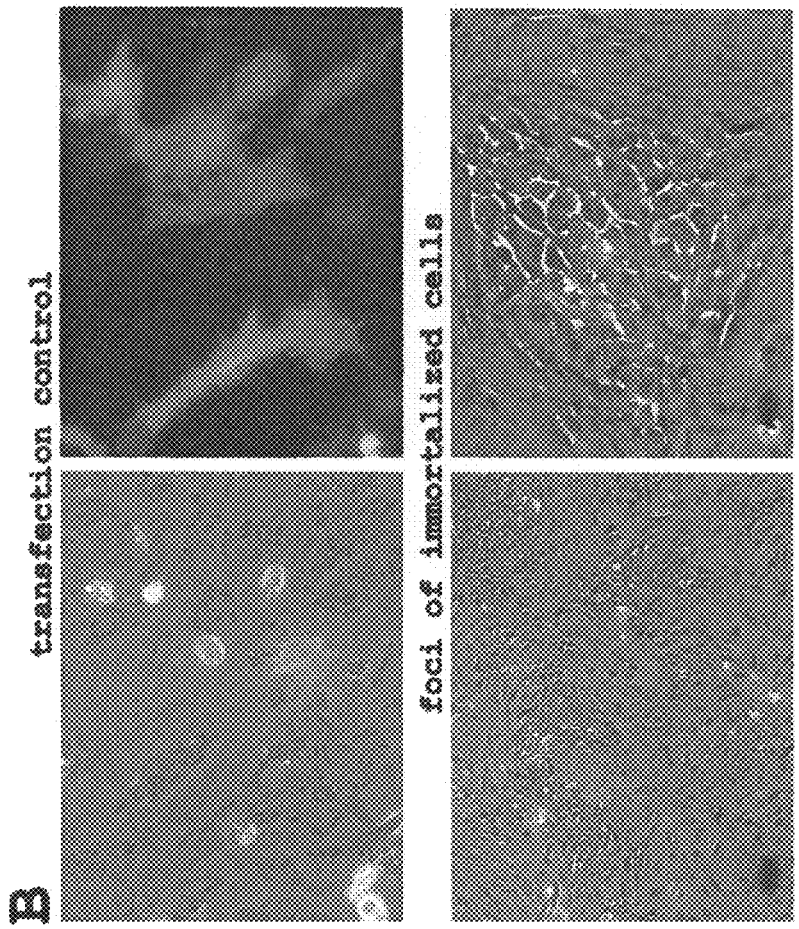

FIG. 2: (A) Plasmid used for immortalization of primary *Rousettus* cells. Shown are functional elements (E1A and E1B genes), location of expression cassettes (driven by human EF promoter for E1A and thymidine kinase promoter of herpes simplex virus for E1B). Also shown are target sites for restricion enzymes used to linearize plasmid prior to transfection. The plasmid is not equipped to express any selection markers in eukaryotic cells. (B) GFP positive control in upper panel to demonstrate successful transfection of primary cells. Foci of immortalized cells in lower panel still embedded in multitude of primary cells.

Figure 3:
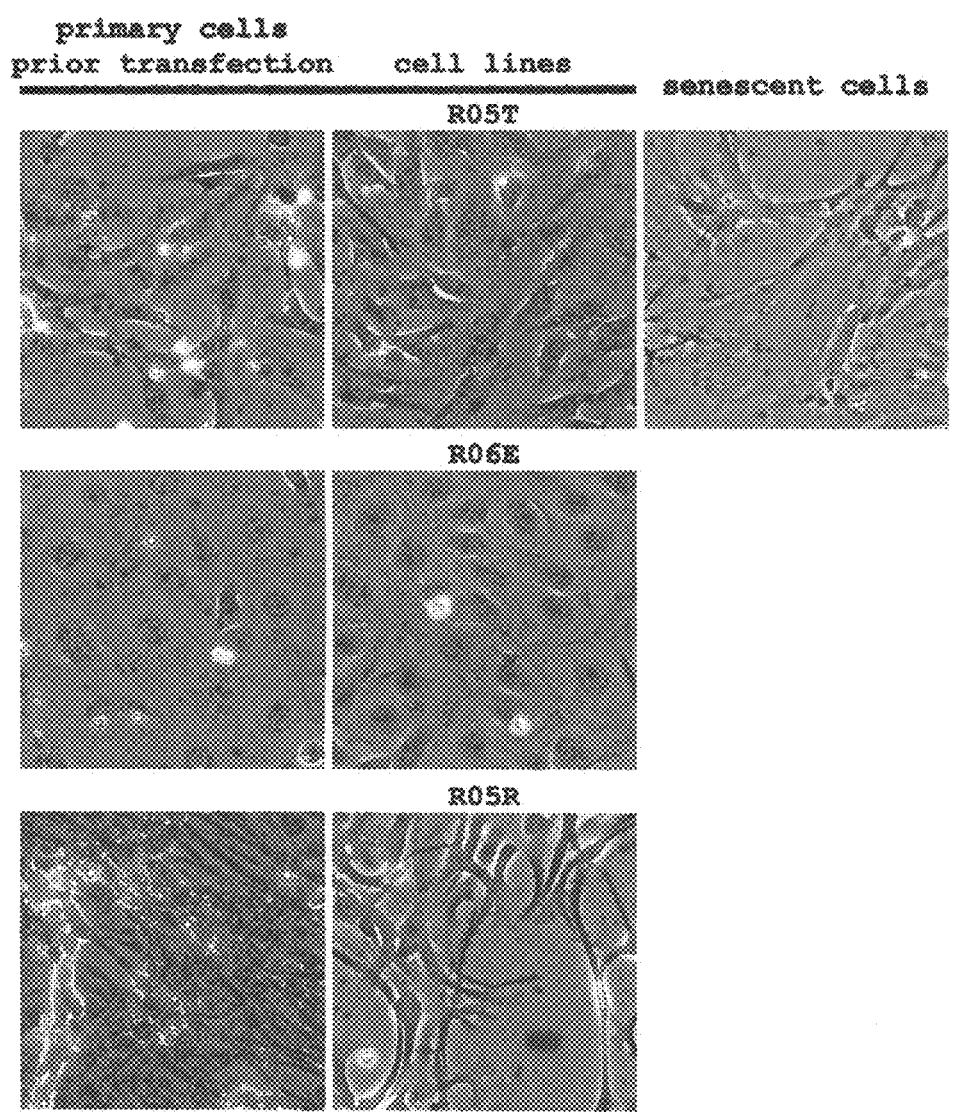

FIG. 3: Appearance of cell lines after immortalization surprsingly resembles morphology and growth properties of the source material. Also shown is a senescent cell that does not proliferate and is lost with passaging of the established *Rousettus* cell lines. Note highly unusual neuronal cell line in bottom panel.

Figure 4:
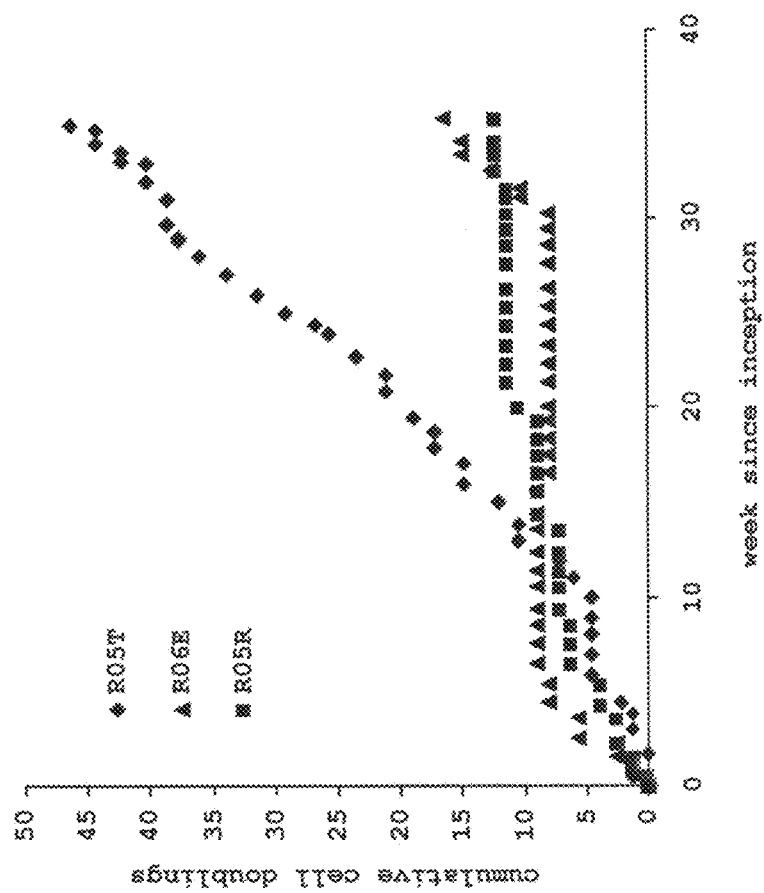

FIG. 4: Early passage history of three of the established cell lines. Note differences in cell proliferation rates that increase for R06E at week 30. The neuronal cell line R05R does not exhibit strong proliferation.

Figure 5:
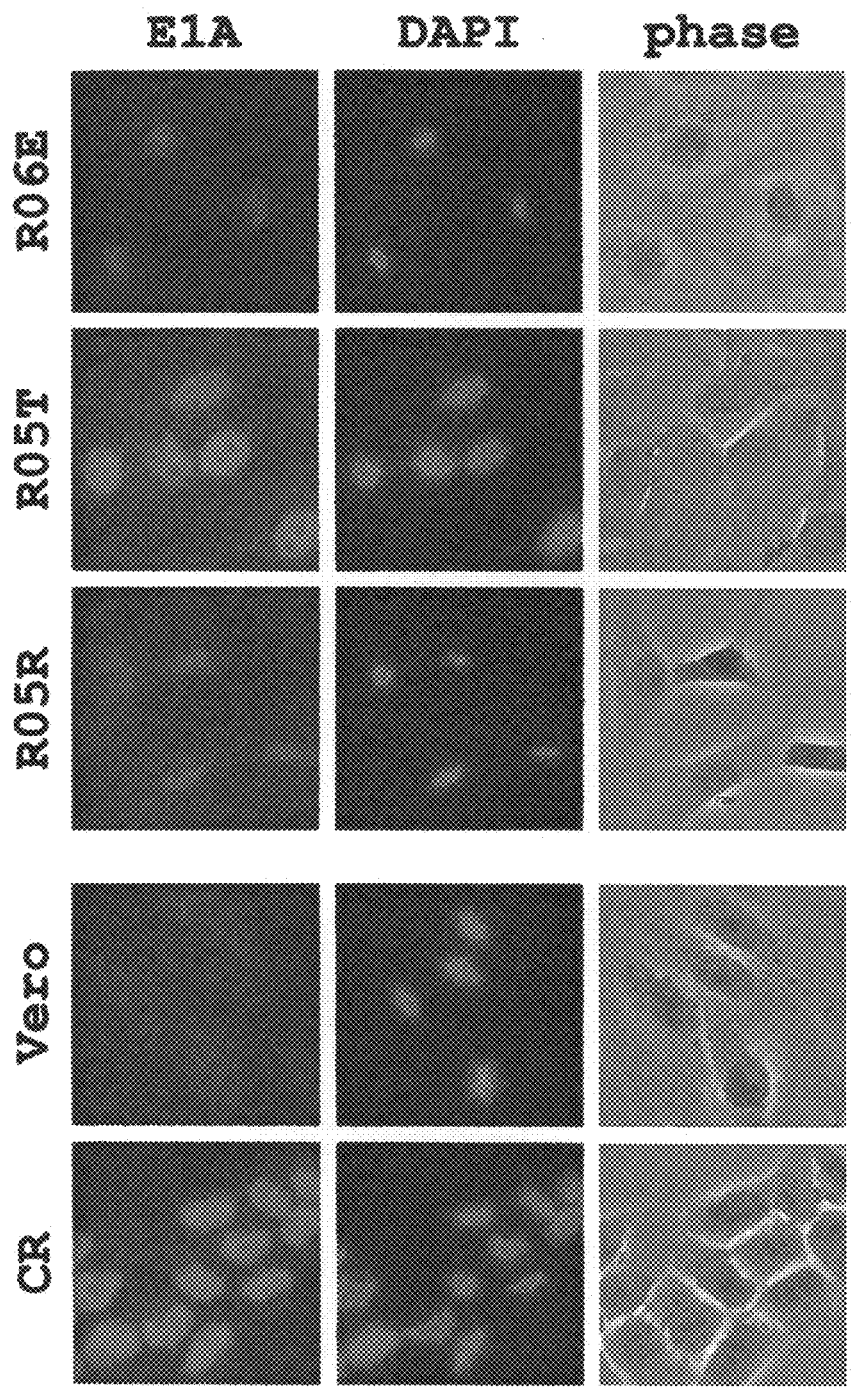

FIG. 5: Immunofluorescence of *Rousettus* cell lines R05R, R05T and R06E demonstrating successful stable integration of expression plasmid for E1 genes. All cells are positive for E1A although expression levels are surprisingly low. CR also expresses adenovirus E1A genes and serves as positive control, Vero cells as negative control.

Figure 6:
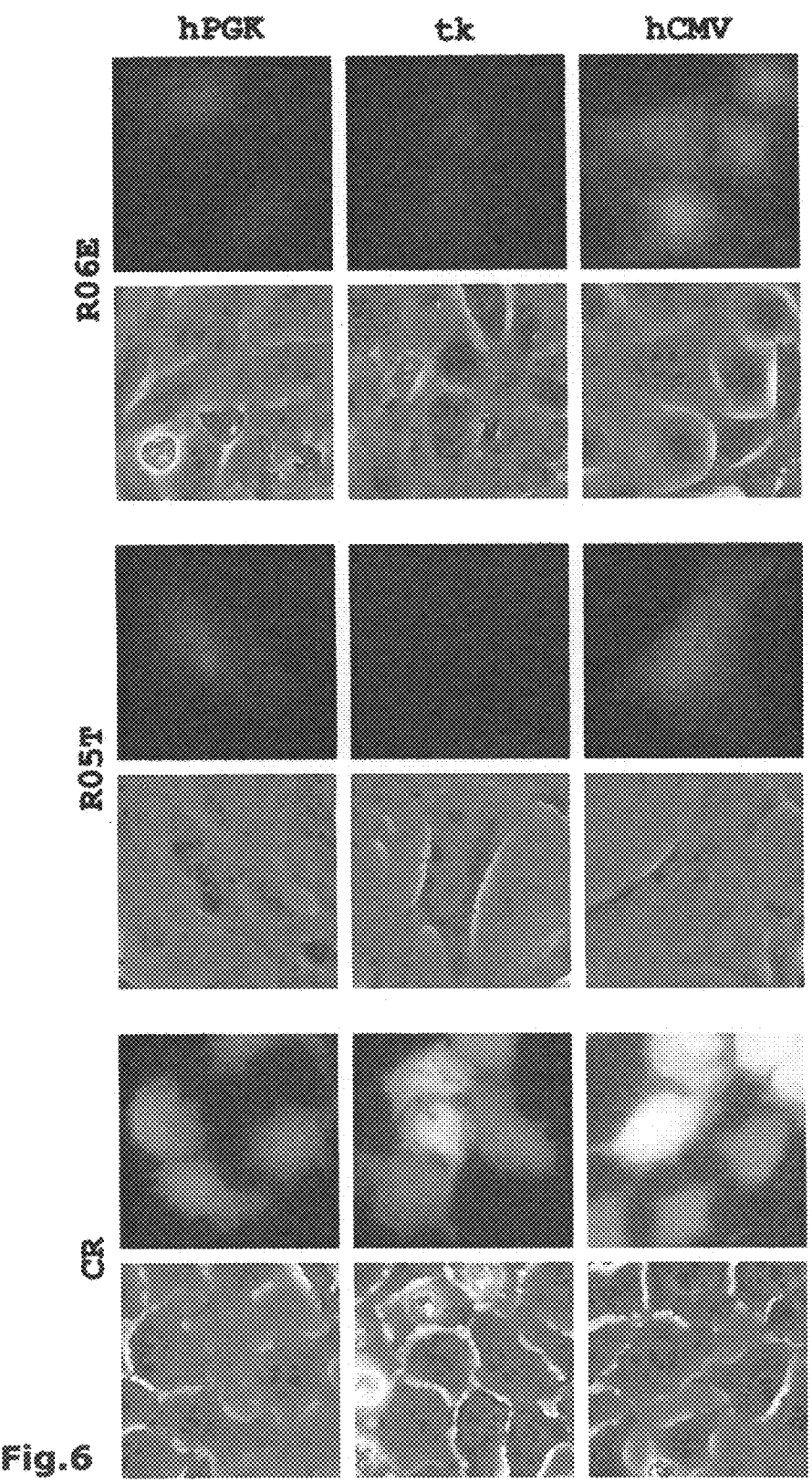

FIG. 6: Comparision of expression strength of the promoters used in the immortalizing plasmid. PGK promoter in plasmid #56G drives E1A expression, tk promoter drives E1B expression. In this figure, the two promoters drive expression of GFP reporter protein. CMV promoter known for very high transient expression levels provides an upper limit. Note extremely low signal strength for PGK and tk promoters in *rousettus* cells but not in CR cells. Even the hCMV promoter activity appears to be repressed in *rousettus* cells. These images were taken 24 h post transfection.

Figure 7:
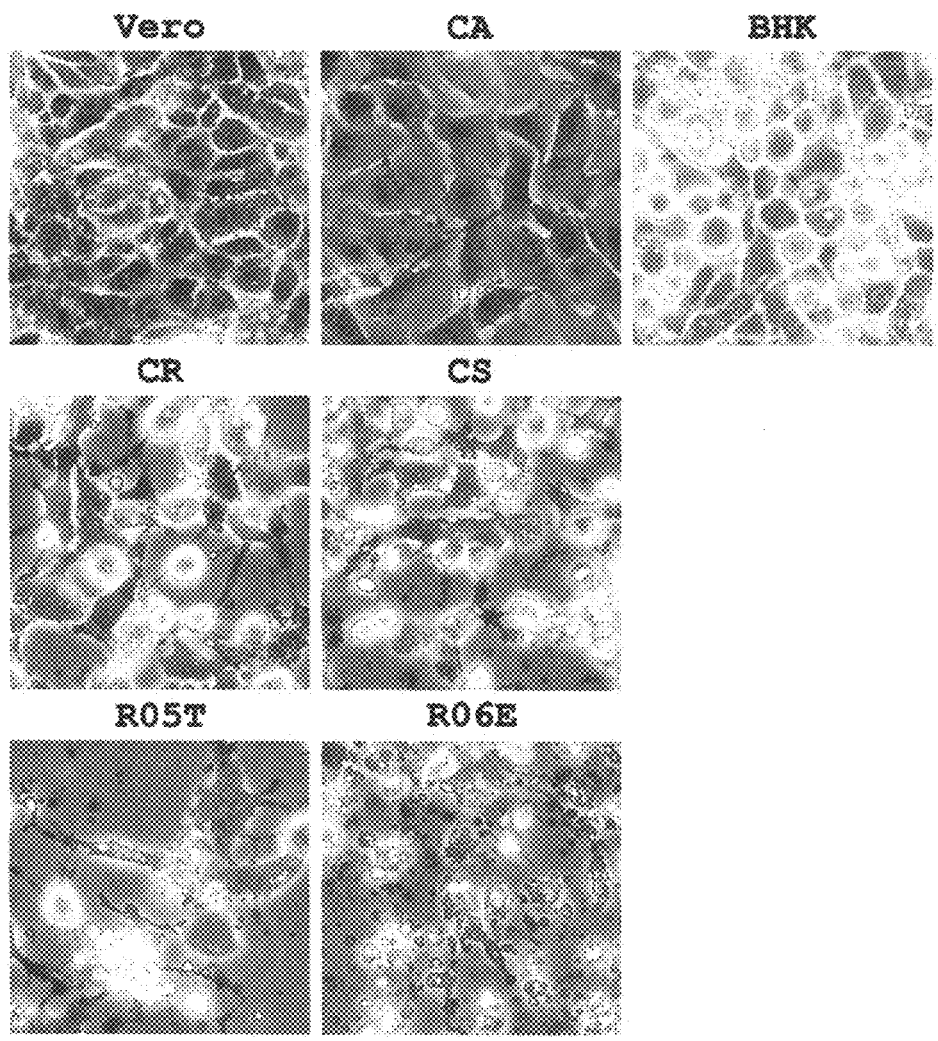

FIG. 7: Appearance of cytopathic effect after infection with modified vaccinia Ankara at a multiplicity of infection of 0.1. Note heavy damage to cell layers in highly susceptible avian (CR and CS) and *Rousettus* (R05T and R06E) cell lines.

Figure 8:
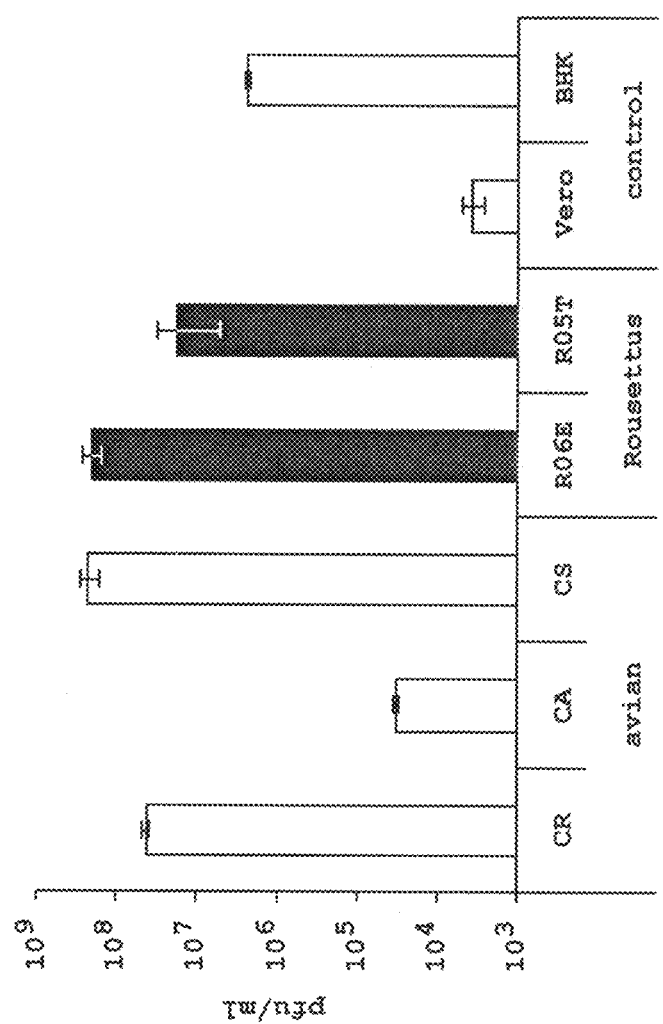

FIG. 8: Yields for MVA on various cell lines.

Figure 9:
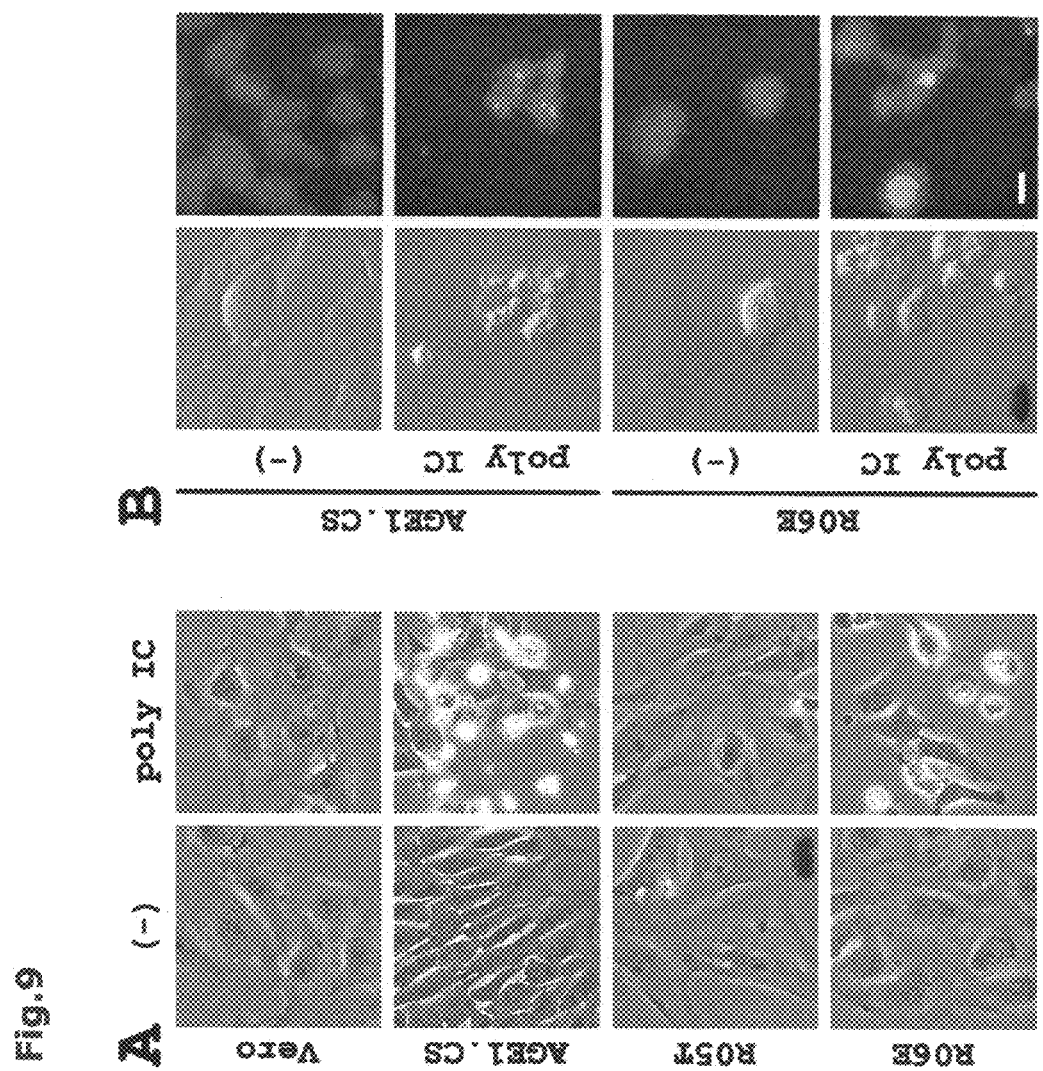

FIG. 9: The *Rousettus* cell line R06E is susceptible to induction of antiviral pathways by poly(I:C) chemical inductor. CS also is susceptible and serves as positive control, Vero is known to be refractory and serves as negative control.

Figure 10:
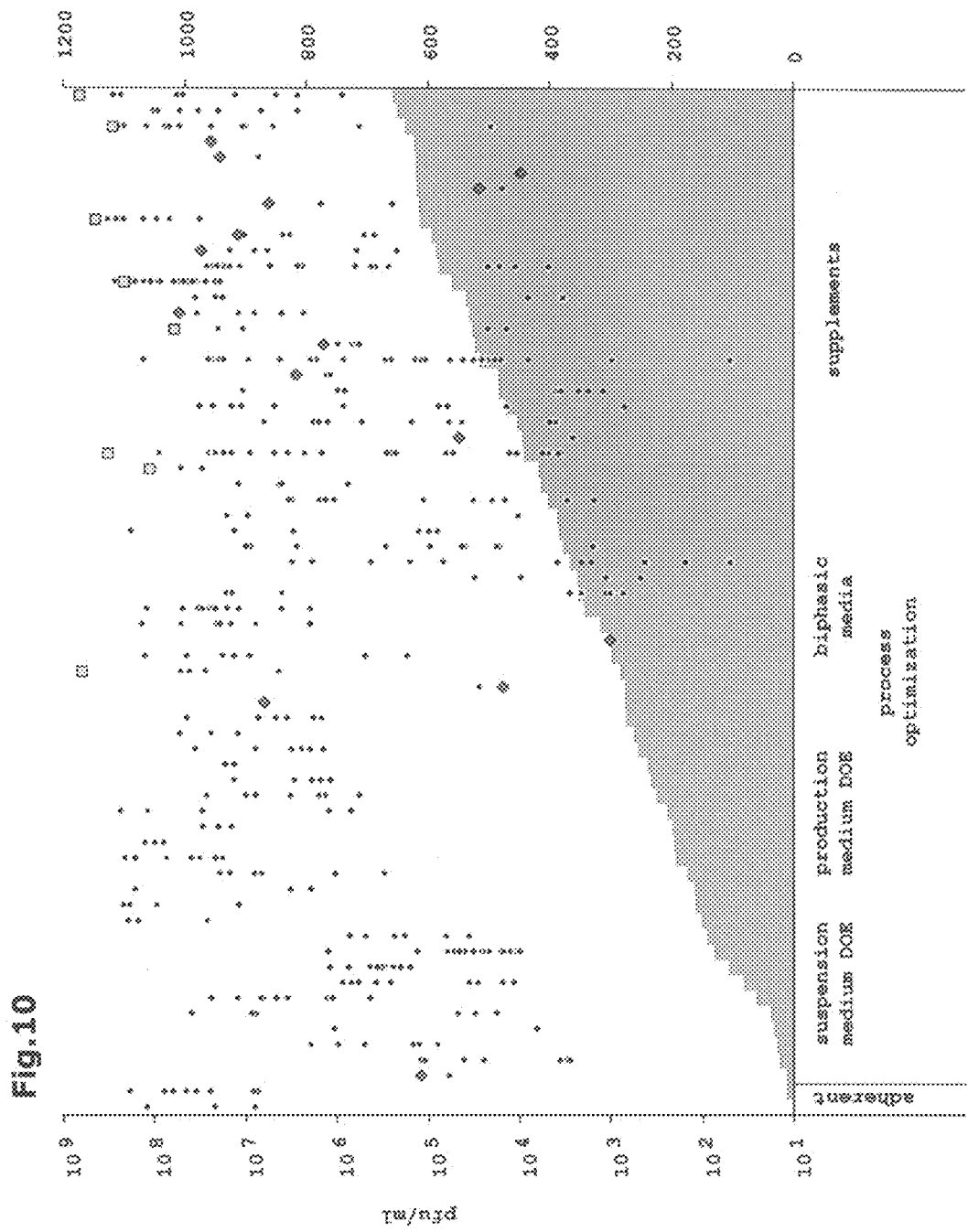

FIG. 10: Optimization matrix for development of a virus production process. The abscissa shows progress of the development in distinct phases, the ordinate improved yields of virus as the process improves. The diamond symbols denote scaleup to Wave bioreactor. DOE, design of experiment, a statistical approach not successful here to combine proliferation and virus production in a single formulation.

FIG. 11: MVA production in media free of animal-derived components. R06E cells were exposed to MVA at an MOI 0f 0.1 and yields were determined 55 hours post infection. Panel A shows appearance of cells in monolayers cultivated in DMEM/F12 with 5% FCS in (a), in suspension medium with 25 mM NaCl in (b) and in fully supplemented suspension medium in (c). Upper row of images is reference culture, lower row depicts infected cells just prior harves. Note absence of cytopathic effect and low titers in (b), robust cytopathic effect and high viral titers in (a) and (c).

FIG. 12: Spread of AdGFP in monolayers of R06E and R05T cells compared to HEK 293 and AGE1.CR. *Rousettus* cells are permissive for human adenovirus vector (compare spread of GFP signal to CR) but resist strong GFP expression and have delayed infectious cycles (compare to 293). Lysate of infected transferred to 293 cells demonstrates limited production of virus in *rousettus* cells. Occasional transfer of AdGFP from CR cells is input-virus carry-over and defines the background in this procedure. The phase contrast images demonstrate homogenous cell monolayers.

FIG. 13: AdGFP replicates in *rousettus* cells and is transferred by co-cultivation. R06E cells were infected with AdGFP at high MOI, passaged at least three times, then mixed at a ratio of 1:1 with HEK 293 cells after the third and fourth passage, respectively. There is transfer of AdGFP to the highly susceptible HEK 293 cells but efficiency of transfer is low and decreases with passaging of the infected *rousettus* culture. Although *rousettus* is permssive for AdGFP it initially is not inhibited or killed by AdGFP even if subjected to very high MOI.

FIG. 14: Susceptibility of R06E cells for AdGFP appears to be affected by degree of purification of inoculum. Whereas R06E clearly is susceptible upon infection with CsCl-purified virus AdGFP given as crude lysate to R06E fails to launch efficient infection. The phase contrast images demonstrate that the lysate is not toxic to the cells. HEK 293 cells are susceptible to AdGFP independent of formulation.

DETAILED DESCRIPTION OF THE INVENTION

"Immortalized", "immortalized cells" and "immortalized cell line" according to the present invention relates to a cell or cell line which has been transfected/transformed by certain functional DNA sequences conferring the potential for at least 200 passages, preferably unlimited number of passages, i.e. immortality, to the respective starting cells.

Cells intended for pharmaceutical purposes such as vaccine or vector production should fulfill a set of strict requirements to minimize risk to recipients (Guidance for Industry, FDA/CBER in September 2006). Most important is compatibility with the Defined Risk Approach (DRA), an algorithm that attempts to estimate risk to recipients of therapeutic proteins or vaccines from certain facts about a cell line such as nature of source material, mechanism of immortalization, tumorigenicity, and characterization for adventitious agents and endogenous retroviruses. It is highly desirable to generate a bat cell line that is compatible with these requirements. The cell line of aspect (i) of the invention fulfills said requirement.

The first steps towards an immortal cell line are extremely important. A cell line should not be derived from a natural tumor or by repeated passaging until a spontaneous transformation event has occurred (or been induced with chemical carcinogens) unless the lesion within the biochemical network is fully characterized and exhaustively determined. The reason is that often vaccines are only minimally purified to maintain viability of the therapeutic component and thus may become contaminated with genomic sequences or protein or mobilized elements from the host cell. The molecular transformation mechanism in spontaneous or natural tumors often cannot be completely elucdiated. The risk from transfer of an unknown mutated oncogene or oncovirus cannot be estimated and justified especially in the light that vaccines often are given a healthy population at a very young age.

For research purposes it is also desirable to know what biochemical pathways have been affected in generation of a cell line.

Immortalization by designed and focused manipulation of biochemical pathways, either by knowledgeable insertion or activation of factors or deletion of cellular mechanism, is compatible with defined risk approaches. To minimize risk, the manipulation should preferably affect or introduce factors of low aggressivity, for example oncogenes that are not pleotropic to an extent that immortalization, transformation, self-sufficiency with respect to growth factors, and metastasis are mediated by a single event. The factor or manipulation should preferably avoid to induce mutagenesis in the host genome.

For example, SV40 polyomavirus large T antigen is a multifunctional protein which affects both checkpoint control in G1 of the cell cycle and p53 activity. Therefore, large T readily immortalizes and transforms multiple mammalian tissues of rodent and human origin. Therefore, this approach is considered aggressive.

Often induction of cell cycle progression (a required event for generation of a stable cell line) induces apoptosis as innate defense mechanism of multicellular organism. We have decided to introduce two new genes that affect checkpoint control of the cell cycle and induction of apoptosis via separate factors: a required simultaneous transfer event of two distinct factors for transformation dramatically decreases any theoretical risk for the vaccinee. An identical desired effect may also be obtained by deletion of cellular genes, for example by knock-out or insertional mutagenesis of the apoptosis mediator and concomitant introduction of the factor affecting cell cycle control.

We have chosen to immortalize bat cells with the E1-gene from human adenovirus serotype 5. Adenoviruses (AdV) are well characterized, naked (non-enveloped) ubiquitous viruses. For the most common serotypes Ad2 and Ad5 the seroprevalence in the human population approaches 90%. Replication incompetent versions of these viruses are used as gene therapy and vaccine vectors in trials with human patients. Genes from the E1 region of human Adenovirus 5 have been used to transform some specific human cells in vitro (293 and PER.C6 cell lines; Fallaux, F. J. et al., Hum. Gene Ther. 9:1909-17 (1998); Graham, F. L. et al., J. Gen. Virol. 36:59-74 (1977)). Mammalian E1-transformed cell lines have been used for the production of live purified adenovirus vectors in clinical trials. With careful monitoring of the amount of contaminating cellular DNA in a vaccine preparation and its size, the transforming genes of Ad5 are not considered a safety hurdle (Vaccines and Related Biological Products advisory committee, session from May 16, 2001).

The general process is inefficient compared to stronger multifunctional oncogenes such as SV40 large T antigen. Based on the observation that HEK 293 cells show neuron specific markers and PER.C6 are of neuroectodermal origin it was suggested that Ad5 E1-based transformation is limited to neuronal cells (Shaw et al. Faseb J 16(8): 869-71 (2002)). We have observed in earlier experiments that immortalization of human cells with E1-genes induces a shift in gene expression towards epithelial patterns (Sandig and Jordan 2006 in Drug Testing In Vitro, ed. Marx and Sandig, WILEY-VCH, Weinheim, chapter 7). Obtaining three cell lines of different morphologies (fibroblast, endo/epithelial and neuronal) is surprising and may reflect a property of chiropteran cells. Especially rescue of a cell line that in morphology and growth kinetics indicates that a neuronal cell line has been generated is an achievement considering the well known difficulties in maintaining primary neuronal cultures (for example, see Brewer and Cotman 1989, Brain Res. 494, 65-74, who employ hypoxic culture techniques in presence of anti-oxidants in extremely small culture volumes).

Adenoviruses replicate in the nucleus of the infected cell. Because quiescent host cells are not permissive for a full viral life cycle adenoviruses have evolved mechanism to force cells into S-phase. To maximize burst size of progeny viruses they have also evolved mechanism to evade apoptosis as a response of the host cell to capsid penetration and viral replication. The genomic region that mediates both cell cycle progression and inhibition of apoptosis is the E1 region.

The E1 region actually consists of two distinct expression cassettes, E1A and E1B, arranged in tandem and each equipped with its own promoter and polyadenylation site. At least three proteins are translated from the E1A primary transcript by alternative splicing. Among others, E1A proteins have been found to disrupt RB/E2F complexes and to interfere with the p300 and CBP transcriptional co-activators. The escape of E2Fs from the RB repressor induces progression of the cell cycle from G1 to S phase, whereas the E1A/p300 complex induces apoptosis via several pathways (Putzer, B. M. et al., Cell Death Differ. 7:177-88 (2000)), including repression of transcription of MdM2, a negative regulator of the key sensor for apoptosis, p53.

As E1A sensitizes cells to TNF-induced apoptosis it is considered an antitumor agent, and it is used in experimental approaches for tumor treatment (Lee, W. P. et al., Cancer Res. 63:6229-36 (2003)).

Furthermore, acting as a transcription modulator it drives cells towards dedifferentiation, a feature advantageous to a potential cell substrate.

The E1B region encodes two open reading frames on a bicistronic mRNA, the 21K and 55K proteins. The 55K protein binds to p53 and thus turns the pro-apoptotic transcriptional activator into a repressor. The 21K protein complements this anti-apoptotic activity by binding to Bax, thus maintaining integrity of the mitochondrial membrane and preventing the release of cytochrome C. This protein is essential to drive adherent cells towards substrate independent growth and hence is essential to a fermentation process in suspension.

Although the underlying mechanism for transformation by E1 is complex one hallmark is a most desirable feature: E1A is a strong inducer of cell proliferation and apoptosis whereas E1B proteins efficiently interfere with apoptosis but cannot release restriction on cell cycle control.

Hence, not a single factor but the continuous presence of E1A and E1B proteins are required to sustain the experimentally induced transformed phenotype. To our knowledge there are only two microbat cell lines known: TB-1 Lu (ATCC number CCL-88) isolated in 1965 from the lung of Tadarida brasiliensis and Mvi/It (ATCC number CRL-6012) from a skin tumor of *Myotis velifer incautus*.

No megabat cell line is currently avaialable. This is regretable as megabats, but not microbats, appear to be the main reservoir for Ebola and Henipaviruses (and probably other pathogens as well). A cell line from a megabat is highly desirable. Generation of a megabat cell line is impeded by a limited supply of primary tissue from which cells can be isolated, in particular less differentiated embryonic material. Generation of a permanent cell line from embryonic stem cells or by extended cultivation of primary cells (with or without concurrent chemical or physical mutagenesis) requires large amounts of donor material because multiple mutations are required to maintain cell cycle progression without induction of apoptosis, senescence or terminal differentiation. Even successful directed immortalisation with a combination of weakly tumorigenic genes targeting individual pathways is a very rare event. The derivation of the first permanent megabat cell lines is, therefore, a suprising phenomenon and was possible using the sophisticated technology described here. To have obtained such cell lines is even more surprising considering strong suppression of expression from transgene promoters as demonstrated in example 2. This fact may have contributed to the observation that the obtained cell lines highly resemble the primary material they have been derived from: it appears as if expression levels of E1A and E1B are just sufficient to maintain immortalization without inducing further differentiation, an unexpected and valuable phenomenon with extremely low probability (possibly the first publication of such an observation).

According to a preferred embodiment of aspect (1) of the invention, the cell line is derived from a primary bat cell. Particularly preferred are fetal or neonatal cells, in particular from neuronal tissue. According to a further preferred embodiment, the cell line is derived from a fruit bat (Megachiroptera), preferably from a *Rousettus aegyptiacus*. Wild fruit bat were not utilized as donors, but *Rousettus aegyptiacus* fetuses were received as a gift from a healthy population at the Wilhelma Zoo in Stuttgart, Germany. The Egyptian fruit bat is of a dark brown or reddish brown fur color with a paler shade on the underside. Typical for a megachiropteran, the Egyptian fruit bat has large eyes, a long fox-like muzzle and the face is without prominent features such as nose leaves. Adult bats are up to 15 cm long with a wing span of 40 cm and body weight of 85 to 175 grams. The Egyptian fruit bat is not endangered, breeds readily in captivity and is considered a pest in some regions in the Middle East.

Fetal cells were immortalized by liposomal transfection of expression plasmids for E1 genes. Retroviral transduction was not performed as this procedure is difficult to reconcile with DRA as genetic elements may become mobilized by long terminal repeats.

Transfected cells were cultivated until primary cells died from senescence and culture shock leaving foci of immortalized cells. These were analyzed by immunofluorescence for E1A protein: all cells that could be passaged beyond the life span of primary cells are E1A positive indicating desired targeted (rather than spontaneous) transformation.

In a particularly preferred embodiment of aspect (1) of the invention the cell line is a primary cell of *Rousettus aegyptiacus* immortalized by an adenoviral E1 gene, preferably is a fetal cell carrying nt 3524 to nt 8361 of SEQ ID NO:1, most preferably is cell line AGE1.R06E as deposited under DSM ACC2902.

An important property of cells intended as diagnostic tool for infectious diseases or as producer cell for vaccine viruses is the complexity and strength of the innate immune system. A strong innate immune system may render the cell refractory to a number of pathogens and would interfere with attenuation (although species-dependent attenuation still would be available). The innate immune system relies on a number of molecules adapted to recognize molecular signatures of common pathogens. These signatures (or patterns) are chemical compositions usually not found in the healthy organism such as lipopolysaccharides of the bacterial cell wall or double stranded RNA as a byproduct of viral replication. The sensors for these patterns are encoded in a superfamily of genes (together with interleukin 1 receptors) that are called are toll-like receptors (TLRs). Each TLR is a sentinel for a specific pathogen-associated pattern and ultimately communicates detection into the interferon type I pathway. Interferon type I is a paracrine and autocrine factor that mediates death of an infected cell via protein synthesis shutdown, RNA degradation, and other mechanism if a pathogen persists.

Reading the literature one may be tempted to assume that the innate immune system of bat cells is not unique: TLRs constitute an ancient gene family present already in prototypical vertebrates with their function as sentinels for pathogen associated patterns (Roach et al. 2005 in Proc. Natl. Acad. Sci. U.S.A. 102, 9577-9582). The interferon signaling cascade into an important effector, the 2'-5' oligoadenylate synthetases, is present even in birds and components thereof have been found reptiles and amphibians (Kumar et al. 2000 in Mol. Biol. Evol. 17, 738-750).

Indeed, primary bat cells react with interferon expression to induction with polyinosinic-polycytidylic acid (poly IC) (Omatsu et al. 2006 in Comp. Immun. Microb. & Inf. Dis. 30, 357-374). Poly IC is an artificial double stranded RNA molecule and as such a surrogate pathogen-associated pattern molecule.

Bat cells apparently are not compromised in their innate immune system. Indeed, they efficiently suppress spread of adenovirus vector after an initial phase of permissiveness (see example 6) and appear to depress activity of promoters on foreign DNA (see example 2) suggesting that they are especially proficient in unspecific defence against pathogens. This ability possibly drives pathogens into occluded chronic infection and thus may help to turn chiropterans into efficient disease vectors. Thus, investigation of aspects of the innate immune system should be highly rewarding using the cells provided here, possibly leading to new therapeutic applications (transferring these mechanism to human patients) or means to control animals in disease carrier states (weakening the resistance of chiropteran to certain diseases so that sick animals are killed before they spread disease). In light of these results it therefore comes as a tremendous surprise that the highly attenuated MVA virus replicates to excellent titers in bat cells. The levels obtained with MVA on *Rousettus* cells exceed the titers obtained with chicken embryo fibroblasts, the host cell MVA has been adapted to in the course of over 500 passages.

To our knowledge it has never been attempted and described to grow a poxvirus in bat cells, especially not the highly attenuated MVA virus.

MVA is attenuated to such an extent that it cannot replicate in human cells. However, it induces a strong immune response in the human organism and therefor is one of the most promising tools for therapeutic and protective vaccine applications even in immunocompromised patients such as HIV-infected individuals with clinical AIDS or immunosuppressed cancer or transplantation patients.

MVA was generated from vaccinia (cowpox) virus by passaging the virus more than 500 times in primary chicken fibroblasts. During the process a number of mutations and deletions in the viral genome accumulated resulting in severe host restriction. Except for avian cells only BHK-21 (baby hamster kidney) has been shown to be permissive for MVA (Drexler et al. 1998 in J. Gen. Virol. 79, 347-52).

MVA is commercially produced in primary fibroblasts isolated from embryonated chicken eggs. Chicken eggs used for human vaccine production must be certified to be free of a defined set of viral and bacterial contamination (specific pathogen-free or SPF). SPF embryonated eggs are expensive and can constitute up to 40% of the cost of vaccines. It is difficult to continually maintain SPF flocks completely free of pathogens which is evidenced by periodic outbreaks of disease in these flocks. Chicken embryonic fibroblasts are prepared from SPF eggs by mincing embryos to establish and amplify viable cells. Typical for primary animal cells the fibroblasts suffer senescence: the doubling time increases with passaging and eventually all cells die. This process occurs after about 20 passages, much earlier than for rodent or some human cell substrates currently used in vaccine manufacture (such as MRC-5 or WI-38). Fibroblast cultures have to be maintained in the presence of 5-10% fetal calf serum, adding additional risk factors to the manufacturing process. They also require a solid surface for propagation and do not grow in suspension, a preferred state for bioreactor applications. Due to the limited live span a complete set of safety tests has to be applied for each lot of chicken fibroblasts.

A pharmaceutically accepted avian cell line is not yet available although at least one such cell line has been characterized to such an extent that it should be clinically acceptable soon.

BHK-21 easily grow in large fermenters on carriers under serum-free conditions (Pay, T. W. et al., Dev. Biol. Stand 60:171-4 (1985); Gallegos Gallegos, R. M. et al., Arch. Med. Res. 26:59-63 (1995)). The BHK-21 cell line is accepted for production of certain vaccines for livestock animals (Lubiniecki, A. S., Bioprocess Technol. 10:495-513 (1990)). However, the BHK-21 line does not meet the safety requirements for human live vaccines. BHK cells have spontaneously formed, are highly tumorigenic and their history is inadequately reported.

Even more significantly: the MVA titers obtained with BHK-21 were significantly lower compared to the yield obtained with chicken embryo fibroblasts. Because MVA does not replicate in the human organism it must be given at high doses to recipients. Current estimates are $10^8$ infectious units/dose. The titers reported on BHK-21 are in the range of only $10^6$ infectious units/ml.

An additional cell line suitable for clincall production of MVA would be highly desirable. To have an additional line available from a host other than birds would provide unexpected potential to therapeutic procedures and attenuation regimes of MVA. However, a cell line permissive for a virus or viral vector is not sufficient in clinical research. Especially for clinical application it is preferred to avoid production and formulation of therapeutic material in presence of animal derived components in culture media, processing solutions and storage buffers.

Production of viruses and microbial vectors without serum supplementation is not trivial and sometimes requires enormous optimization matrices. Adherent and suspended cells differ fundamentally in many properties important for the viral infectious cycle. For example, a suspended spherical cell suffers changes in the cytoskeleton or loss of cell polarity, and this may interfere with virus adsorption to selected cell membranes, morphogenesis and migration along actin filaments, and release from specially equipped cell surfaces. Furthermore, formulation of suspension media are optimized towards proliferation in absence of cell aggregates. Such a single cell suspension can be adjusted with surfactants, various polymers, salt and lipid composition in the medium. The suspension medium formulation changes the properties of plasma membranes (and viral envelopes) such that repulsive forces dominate that also interfere with adsorption of virus. Furthermore, tight cell contact in aggregates may facilitate spread especially of enveloped viruses that sometimes have extracellular and cell-associated infectious forms. Especially for the orthopoxviruses (including MVA) maturation is complex and different forms of enveloped and cell-associated or liberated infectious virions co-exist in the viral life cycle (reviewed in Smith et al. 2002 in J. Gen. Virology 83, 2915-2931). And yet, for many technical reasons including efficient lysis of infected cells and downstream processing, it may be preferred to have a process with homogenous cell distribution rather than aggregate formation.

Another important point to consider is cell cycle and metabolism of the host. An infected cell has different metabolic requirements than a proliferating cell and suspension media often do not provide the required amount of energy and nutrients to consistently support virus replication. Furthermore, in media free of animal-derived components self-conditioning of the medium is especially important and also for this reason suspension cultures require higher starting cell densities than adherent cultures. Greatest yield of virus or microbial vector is obtained in late phases of the process when the second or third generation is released but cell proliferation reaches its plateau. At the same time, nutrients become limited and catabolites accumulate causing shifts in pH and complicated biochemical signal cascades feeding back into the cell metabolism. To control such parameters is important for production of recombinant proteins but especially critical in virus production processes that usually are initiated with low MOIs.

Furthermore, macromolecular interaction is crucial. The interaction of viral membranes of enveloped viruses with cell membranes is similar to the interaction between cells. We have observed that common proliferation media, in particular those formulated for suspension culture free of animal derived components interfere with production of enveloped viruses, in particular poxviruses (for example MVA) but also togaviruses and lyssaviruses. This interference occurs irrespective of whether these media are compatible with production of non-enveloped viruses such as adenovirus.

It was surprisingly found that using suspension culture media a production process for enveloped viruses, in particualar the poxvirus MVA, can become feasible by supplementation with commercially available charged or uncharged polymeres such as (but not limited to) poly[imino[(2S)-2-amino-1-oxo-1,6-hexanediyl]] at 0.001-0.01% (w/v); poly[1-(2-oxo-1-pyrrolidinyl)ethylen] at 0.5-2%; N-[1-(2,3-dioleyloxy)propyl]-N,N,N-trimethylammoniumchlorid at 5-10 µM; 1-oleoyl-2-[6-[(7-nitro-2-1,3-benzoxadiazol-4-yl) amino]hexanoyl]-3-trimethylammonium propane or N-[1-(2,3-Dioleoyloxy)]-N,N,N-trimethylammonium propane methylsulphate at 50-100 µg/ml; 1,5-dimethyl-1,5-diazaundecamethylene polymethobromide at 10-200 µg/ml; linear polyethylenimine at 25-75 µg/ml; polyoxyethylene-polyoxypropylene at 0.001-0.5% (w/v); diethylaminoethyl-dextran hydrochloride at 1-50 µg/ml; poly(D-glucosamine) at 0.005-2% (w/v); glucuronic acid-O-sulfatmucopolysaccharide at 50 to 500 U/ml; or poly-L-ornithine hydrobromide at 0.001-0.01% (w/v).

Furthermore, it was found that ionic strength in the suspension proliferation medium need to be adjusted with inorganic salts, preferably at the time of infection with an MOI below 1.0, for example, by supplementing with 1 volume of calcium chloride at 1.05 mM, cupric sulfate at 0.0000052 mM, ferric nitrate at 0.000124 mM, ferric sulfate at 0.0015 mM, magnesium chloride at 0.3 mM, magnesium sulfate at 0.407 mM, potassium chloride at 4.16 mM, sodium bicarbonate at 14.29 mM, sodium chloride at 120.61 mM, sodium bromide at 2.0 mM, sodium phosphate dibasic at 0.5 mM, sodium phosphate monobasic at 0.453 mM, and zinc sulfate at 0.432 mg/l.

Each supplementation by itself has limited effect on MVA productivity in media free of animal-derived components but in combination the obtained yields approach and often exceed yields observed in cells infected and cultivated in FCS-supplemented basal medium.

Changing contributions of certain properties and interactions of cell and complex microbial agent need to be accommodated especially in a production process that is either completely chemically defined or at least free of animal derived components. Here, a biphasic process is provided for production of enveloped viruses such as MVA. The two phases are a proliferation phase in medium optimized for cell growth in suspension and a virus replication phase that is initated by infection and addition of a combination of the above mentioned components without removal and replacement of the proliferation medium.

The cell line AGE1.R06E was deposited according to the Budapest Treaty with the DSMZ Deutsche Sammlung von Mikroorganismen and Zellkulturen GmbH, Inhoffenstr. 7B, 38124 Braunschweig, Germany on Apr. 3, 2008, it received the Accession No. DSM ACC2902.

The invention is further explained by the following examples, which are, however, not to be construed as a limitation of the invention.

EXAMPLES

Example 1

Immortalization of Primary *Rousettus* Cells with E1 Genes

Fetuses from *Rousettus aegyptiacus* were a kind gift from the Wilhelma Zoo in Stuttgart. FIG. 1 shows steps towards isolation of the fetuses from pregnant bats. The fetuses were separated into head and body and individual cells isolated by brief digestion with TrypLE (Gibco, a trypsin replacement) and tituration into DMEM/F12 medium (Gibco) containing 5% fetal calf serum (Biochrom AG). The cells were seeded into 6-well culture plates and transfected with effectene (Qiagen) within 1 to 1.5 weeks after plating. Cultivation in all of the described experiments was performed at 37° C. and 8% $CO_2$ in the gaseous phase.

The plasmid used for transfection and immortalization designated #G56 (FIG. 2 and SEQ ID NO:1) was constructed in accordance with WO/2005/042728 with genomic human adenovirus sertype 5 sequences from a wild-type contamination in a vector preparation produced on HEK 293 cells: primers ACTCGAGCTGACGTGTAGTGTATT and CACACGCAATCACAGGTT (SEQ ID NO:2 and 3, respectively) were used to amplify the E1A region and primers ACTCGAGTCATGGAGGCTTGGGAGT and ACACATTTCAGTACCTCA (SEQ ID NO:4 and 5, respectively) were used to amplify the E1 B region. Amplification was performed with ProofStart polymerase (Qiagen) and integrity confirmed by sequencing.

Expression of E1A is driven by the promoter for human phosphoglycerate kinase, amplfied from genomic DNA of HEK 293 with primers GAGATTAATGGTTGGGGTTGCGCCTT and AACTCGAGAACGAGGGAGCCGACTGCC (SEQ ID NO:6 and 7, respectively). Expression of E1B is driven by the thymidine kinase promoter of herpes simplex virus.

Prior to transfection #G56 was digested with ApaLI, RsrII and ScaI (all from New England Biolabs) restriction enzymes to linearize the plasmid and to remove the bacterial selection markers. Transfection of primary cells was performed with cells growing as monolayers in 6-well plates with 2 µg of linearized plasmid DNA and 16 µl enhancer in Qiagen-provided EC-buffer. After 5 min of incubation, depending on confluency of the cell layer, 16 µl to 20 µl of effectene reagent was added and this suspension was incubated for further 10 min. Thereafter, the transfection mix was applied to the cell monolayer in a final volume of 1 ml of medium. After 3 hours additional 1.5 ml medium were added, the following day the medium was replaced completely.

Liposomal transfection of primary cells can be difficult. To determine transfection efficiency an expression plasmid for GFP was transfected in parallel (FIG. 2)—transfection efficiency was low but adequate. After approx. 2 weeks in culture foci appeared where cells were more homogeneous in appearance and smaller in size compared to the large and pleomorphic primary cells (FIG. 2). Because primary cells and transfected cells that did not integrate the DNA together constitute the vast majority in the cultures a considerable hurdle in generation of a new cell line is rescue of the clonal populations. We recovered foci by gentle treatment with TrypLE for a time span that allowed detachment of clonal cells leaving most of the primary cells in the flask. Many primary cells still were transferred but were sequentially lost to senescence over a period of approximately six months of continous culture. Senescence describes a cellular state with decreased proliferation rates until complete stasis or cell death due to telomere erosion of the chromosomes and accumulation of signal proteins important in cell cycle control. Senescent cells usually are large and pleomorphic with striated cytoplasm of low phase contrast.

FIG. 3 shows three of the final cell lines after nine months of continous culture in the middle panel. A typical senescent cells is shown in the right panel. Most surprising is the fact that we established three different cell lines of distinct appearance and possibly lineage. The reason for our surprise is based on the fact that E1 immortalization appears to be most efficient in neuronal cells and on an earlier observation suggesting that immortalization of human cells with E1-genes induces a shift in gene expression towards epithelial patterns. We obtained one cell line consistent with epithelial properties and one cell line with fibroblast appearance. Both cell lines highly resemble the source material prior to transfection shown in the left panel of FIG. 3.

Neuronal cells are extremely difficult to cultivate (for example, see Brewer and Cotman 1989 in Brain Research 494, 65-74: they require carefully adjusted hypoxic culture conditions, low culture volumes for self-conditioning of medium and detoxification in absence of supporting glial cells). We did not adapt culture conditions to neuronal cells and to our knowledge it is completely unexpected that neurons continously and without exogenous nerve growth factors or phorbol esters form the long and branched spines as observed in our culture (bottom row of FIG. 3). The primary neuronal cells in the left panel were isolated from the vertebrate of a *Rousettus* embryo, the immortalized neuronal line was obtained by transfection of cells isolated from the head.

Consistent with culturing properties of true neurons the cell line proliferates very slowly and passaging is possible only once or twice per month. FIG. 4 compares a cell line histories in terms of cumulative cell doublings. Each manipulation event including change of medium has been documented and is depicted here for an interval of 35 weeks. Clearly visible is the early and strong proliferation of the fibroblast line, stabilization of the epithelial line approx. 30 weeks after isolation and transfection of primary cells, and the slow but successful cultivation of the neuronal line.

It is a completely unexpected observation of this invention that tissue-specific expression patterns appear not to change on a macroscopic scale in bat cells upon immortalization with E1 genes. This property probably extends to other immortalization strategies.

Example 2

Immunofluorescence Assay for Stable Transfection

Cultures of immortalized cells were seeded on glass slides and allowed to proliferate for several days before fixation with ice-cold methanol for 10 min. The fixed cells were incubated with antibodies against E1A protein, secondary antibodies, and fluorescent dye specific against the latter according to standard immunofluorescene methods (Becton Dickinson, UK, #554155 antibody against E1A, diluted 1:30; secondary antibody directed against mouse and conjugated to biotin, both from Jackson Immuno Research, USA, diluted 1:80; visualization with Jackson Immuno Research, USA, #016-070-084 streptavidin-Texas Red conjugate, diluted 1:100). AGE1.CR cells (duck retina cells; WO/2005/042728) that stably express the Ad5 E1-region served as positive control, BHK cells as negative control. DAPI (4',6-diamidino-2-phenylindol; Sigma, USA) to 1 μg/ml was added in the final incubation step to stain the nuclei of the cells for orientation purposes.

FIG. 5 shows the result obtained with cultures R05T and R06E. A specific signal for E1A was observed in all cells confirming successful immortalization by the transfected plasmids. Furthermore, spontaneous transformation, a formal possibility, was not observed as all cells were E1-positive.

FIG. 6 provides an explanation for weak signal intensity of E1A in bat cells: the GFP reporter protein was coupled to various promoters including hPGK, tk and hCMV. hPGK promoter in plasmid #56G drives E1A expression, tk promoter drives E1B expression. The hCMV promoter is known for very high transient expression levels and thus provides an upper limit. Transfection into the *rousettus* cell lines was performed with liposomal formulation of the plasmids as in example 1. Note extremely low signal strength for PGK and tk promoters in *rousettus* cells but not in CR cells. Even hCMV promoter activity appears to be repressed in *rousettus* cells.

Example 3

Modified Vaccinia Virus Ankara (MVA)

Cells of the *Rousettus* epithelial and the fibroblast cell lines were seeded into 6-well plates infected with MVA (ATCC #VR-1508) at multiplicity of 0.1 infectious units per cell after 24 hours of culture. As positive controls CR and CS (avian cell lines derived from retina and somites) and as negative controls Vero (African green monkey kidney cells; ATCC CCL-81) and CA (avian amniocyte cell line; patent application WO/2005/042728) were infected in parallel. 48 hours post infection a strong cytopathic effect was evident in the positive controls and suprisingly also in the *Rousettus* cell lines (FIG. 7). As expected, no spread of virus and no or minimal cytopathic effect was visible in the Vero and CA cell lines that are refractory for MVA.

This result is unexpected as MVA is derived from vaccinia virus Duke strain by adaptation to embryonated chicken eggs (yielding CVA, chorioallantois vaccinia Ankara) followed by more than 500 passages in chicken embryonic fibroblasts (yielding MVA). MVA is attenuated to such an extent that it cannot replicate in mammalian cells tested thus far with BHK as a single exception. The severe host range restriction is programmed into MVA by a number of mutations and deletions that have reduced the size of the genomic DNA from 200 kb in Duke to 192 kb in CVA down to 178 kb in MVA.

Infected cells were resuspended into the culture medium by pipetting and lysed by three cycles of freeze/thawing to also harvest virus from within the cells. The suspension was cleared by centrifugation and titration was performed on Vero cells (Vero cells do not replicate MVA but they are susceptible and can be infected for titration purposes), briefly: Vero cells were seeded in 96 well plates at $2 \times 10^4$ cells per well and infected with serial 10-fold dilutions of MVA-containing suspension on the following day. Two days thereafter, the cultures were fixed with methanol and incubated with polyclonal vaccinia virus antibodies (Quartett, Germany, #9503-2057, at 1:1000 dilution in PBS containing 1% fetal calf serum) for 1 hour at 37° C. Two wash steps were performed with PBS containing 0.05% Tween 20 (Sigma Corp, USA) and secondary antibody to the vaccinia-specific antibody is added at 1:1000 dilution in PBS containing 1% fetal calf serum. This secondary antibody is coupled to the peroxidase enzyme that catalyzes a color reaction upon incubation with AEC reagent (3-amino-9-ethyl-carbozole; 0.3 mg/ml in 0.1 M acetate buffer pH 5.0 containing 0.015% $H_2O_2$). Infected foci are identified by light microscopy and plaque forming units are calculated from the maximum dilution of MVA suspension that yields a positive dye reaction.

FIG. 8 demonstrates that replication of MVA in *Rousettus* cells is not an artefact but clearly surpasses the published values in the range of $10^6$ pfu/ml for replication in BHK (Drexler et al. 1998 in J. Gen. Virol. 79, 347-52). Yields for MVA in multiplying in the avian cell line AGE1.CS is superior to yields in primary chicken embryo fibroblasts, an accepted production system for MVA. R06E releases similar levels of MVA ($2.3 \times 10^8$ pfu/ml and $2.1 \times 10^8$ pfu/ml, respectively). The R05T cell line is less efficient than R06E but with $3.3 \times 10^7$ pfu/ml in the expected range for a fully permissive host cell and similar in yields to the permissve avian cell line AGE1.CR. Nonpermissive cell lines CA and Vero provide a base line: yields there correspond to input virus or extremely limited replication in the case of the CA line. The literature value for BHK is confirmed in our experiments performed in parallel to the infection of the novel *Rousettus* cell lines: BHK produces less virus than R05T and R06E.

For production purposes of vaccine vectors one often calculates burst rates given by the ratio of yield to inocolumn with seed virus. Burst size is equivialent to amplification of virus and thus important to estimate cost and required resources for large scale production.

For R06E the burst size is 4133 at a multiplicity of infection with 0.1, an excellent amplification for MVA. High amplification rates are especially important for MVA because this vector cannot replicate in the human vaccinée. This is an important safety feature as even immunocompromised patients can receive MVA as therapeutic vaccine. However, lack of replication necessitates vaccination with high doses of infectious particles—most estimates are in the range of $10^8$ infectious units/shot. Providing a mammalian cell line generated according to the defined risk approach that allows economical production of MVA for vaccine purposes is highly desirable.

Example 4

Poly IC

In a recent publication on bat microbiology and epidemiology (Omatsu et al. 2006 in Comp. Immun. Microb. & Inf.

Dis. 30, 357-374) it is strongly suggested "to use primary cell culture [rather] than using an established cell line to evaluate host response to virus or microbes." because the only available bat cell line TB-1 Lu is deficient in response to dsRNA.

dsRNA is one of several pathogen associated patterns a cell uses to identify exposure to parasites. These molecular patterns are recognized by sensor molecules called Toll-Like Receptors or TLRs. TLRs communicate into the interferon type I pathways. These interferons induce an anti-viral state in non-infected cells and apoptosis in infected cells, thus precluding viral replication.

Thirteen TLRs are known, each receptor with specificity for a class of molecular patterns such as bacterial lipopolysaccharides (TLR-4), glycolipids (TLR-2), flagellin (TLR-5), unmethylated CpG-DNA (TLR-9) and dsRNA (TLR-3). If a cell does not respond to a given pattern the innate immune system is compromized, either because of properties of the immortalized source material as different tissues are differently equipped to respond to pathogens, or because the immortalization events have disabled certain biochemical pathways. This apparently has occurred in the TB-1 Lu compromising suitability of this cell line for diagnostic purposes that rely on cytopathic effect and for research where biochemical pathways need to be characterized.

Primary cell cultures are not a desirable alternative to TB-1 Lu: they require continous supply of donor animals which is difficult especially in the case of bats, and often introduce great variations in cell properties with each preparation and as passage number increases.

To determine whether our *Rousettus* cell lines respond to dsRNA we used a common synthetic analogue of viral dsRNA, poly IC (Sigma), and compared effects of treatment with poly IC to a cell line known to be sensitive to TLR-3 induction (AGE1.CS) and to a cell known to be deficient in interferon type I pathways (Vero). Poly IC was added at a concentration of 400 µg/ml directly to the medium of the cells in the presence of fetal calf serum to challenge the TLR-3 receptor; poly IC can also be transfected to interrogate intracellular receptors for dsRNA but this would introduce the molecular pattern downstream of the interferon induction and is a less stringent examination.

Within 8 hours of treatment increased cell death was observed for the CS and the R06E cell lines (FIG. 9, panel A). To confirm that cell death is due to apoptosis the culture was stained with 5 µg/ml DAPI without prior fixation. Fragmented nuclei were observed only in poly IC treated CS and R06E cell lines (FIG. 9, panel B) demonstrating induction of apoptosis and thus intact TLR-3 signaling into the interferon pathways (for example, see DeWitte-Orr et al. 2005 in Fisch & Shellfish Immunology 18, 279-295, and Tanaka et al. 1998 in Genes to Cell 3, 29-37 for demonstration that interferon is required for induction of apoptosis by dsRNA). Failure of R05T and Vero to respond similarily to dsRNA indicates that poly IC per se is not toxic to the cells and that we can both provide a highly desirable novel cell line responsive to at least one pathogen associated molecular pattern (R06E) and another novel cell line from *Rousettus* (R05T) as direct comparision to TB-1 Lu from a microbat.

In conclusion, we generated at least three different cell lines with distinct properties from tissues of *Rousettus aegyptiacus* fetuses. The cell lines are unusual in that they appear to have retained a number of primary features that even extend to a neuronal line. The lines are also unusual in that they are fully permissive for MVA, a highly attenuated virus that usually does not replicate in mammalian cells. Furthermore, at least one of the cell lines is unusual in that it responds with interferon induction to challenge with a pathogen associated molecular pattern.

Bats appear to be unique among mammals because they rarely exhibit clinical symptoms after infection with a variety of extremely virulent pathogens such as Ebola virus, SARS-CoV and lyssavirus. We add a paradox to this observation: bat cells appear not to be especially resistant to pathogens. Rather, they replicate highly attenuated MVA to surprisingly high levels that rival yields obtained on cells of the avian host MVA has been adapted to.

Example 5

MVA Production in Media Free of Animal-Derived Components

Figure 11:
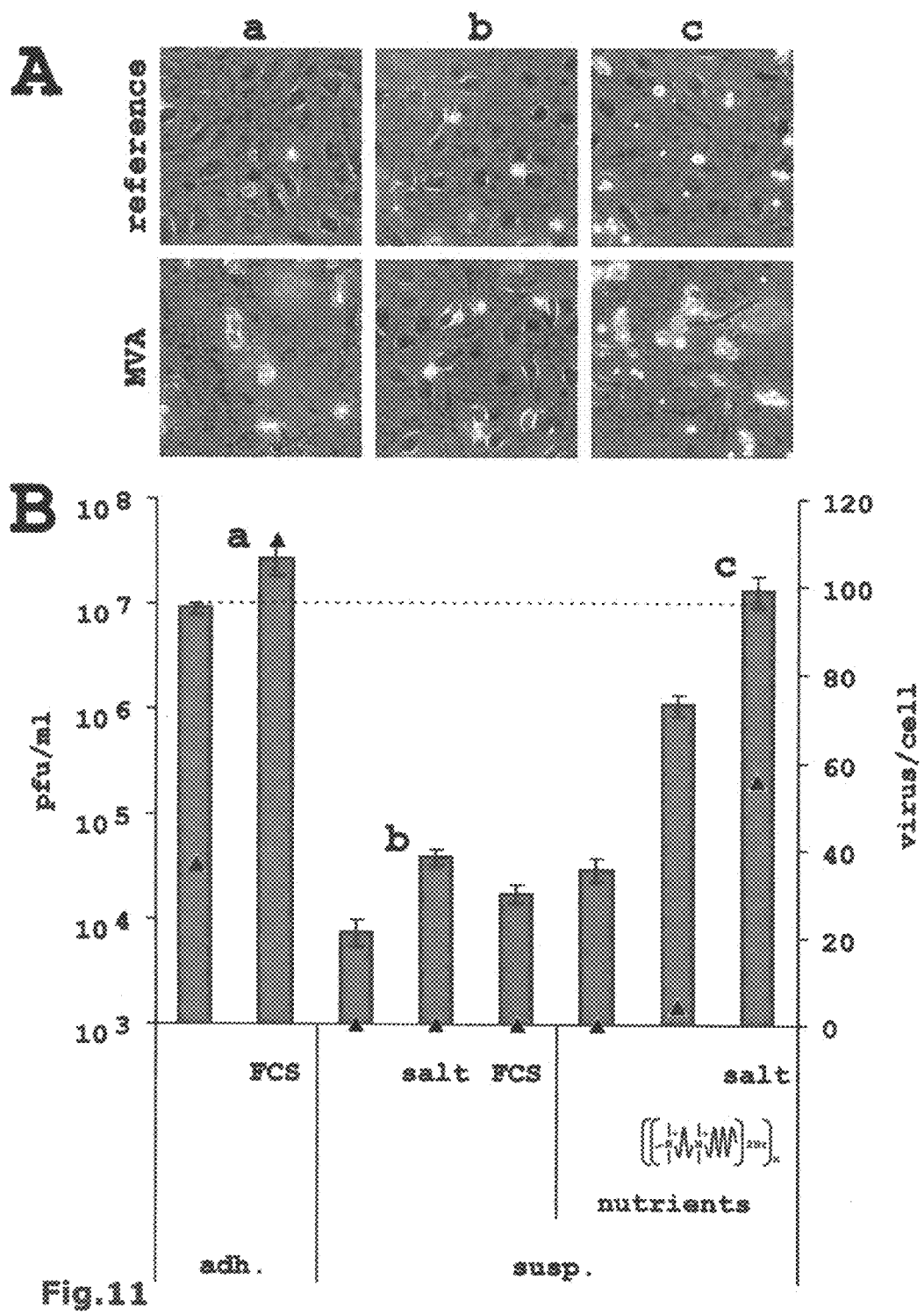

As described above, especially for clinical application it is preferred to avoid production and formulation of therapeutic material in presence of animal derived components in culture media, processing solutions and storage buffers. Given the interest in MVA as vaccine vector production of this virus was assayed in this example with R06E as host cell. The insights gained here can be adapted to other microbial agents and host cells. The medium used as base medium for infection and cultivation of R06E is animal-derived component free and optimized for proliferation in suspension. The bar chart in FIG. 11 is a compacted result of underlying optimization matrices with well over 600 individual titrations (visualized in FIG. 10) and demonstrates in the left panel high productivity for MVA in conventional growth medium for adherent cells such as DMEM:F12 with 5% fetal calf serum (FCS). DMEM/F12 is formulated for supplementation with serum and consequently titers decrease in DMEM:F12 without FCS. DMEM:F12 with or without FCS supplementation is not suitable for passaging of cells, not on microcarriers nor in suspension. If passage in medium free of animal-derived components is desired cells need to be passaged in media specially formulated for such a process. Such media are commercially available and include Gene Therapy Medium 3 (Sigma, USA), ProPER-1 and ProCHO 3 (both from Lonza, Belgium), or Adenovirus Expression Medium (Invitrogen, USA). As discussed above, common proliferation media free of animal derived components may interfere with a virus production process, clearly visible in FIG. 11. MVA yields decrease by three orders of magnitude in suspension media without adequate supplementation. By manufacturer's designation, Gene Therapy Medium 3 and Adenovirus Expression Medium are formulated for adenovirus production. However, adenoviruses are naked viruses. Sensitivity to default suspension medium formulation may be a property of enveloped viruses in general. We have observed vastly decreased yields also for other unrelated enveloped viruses such as togavirus and lyssavirus in common suspension media. Often, considerable effort is necessary to develop a process that allows these enveloped viruses to be produced on a permanent host cell.

In this example, adherent monolayers are shown to better illustrate the effects from viral infection: cultures in unsupplemented suspension medium display no cytopathic effect (compare images (a) and (b) of the infected cells in FIG. 11, panel A). Yields do not increase by supplementation with FCS. An MVA production process can become feasible by supplementation with commercially available charged or uncharged polymeres such as (but not limited to) poly[imino [(2S)-2-amino-1-oxo-1,6-hexanediyl]] at 0.001-0.01% (w/v); poly[1-(2-oxo-1-pyrrolidinyl)ethylen] at 0.5-2%;

N-[1-(2,3-dioleyloxy)propyl]-N,N,N-trimethylammonium-chlorid at 5-10 µM; 1-oleoyl-2-[6-[(7-nitro-2-1,3-benzoxadiazol-4-yl)amino]hexanoyl]-3-trimethylammonium propane or N-[1-(2,3-Dioleoyloxy)]-N,N,N-trimethylammonium propane methylsulphate at 50-100 µg/ml; 1,5-dimethyl-1,5-diazaundecamethylene polymethobromide at 10-200 µg/ml; linear polyethylenimine at 25-75 µg/ml; polyoxyethylene-polyoxypropylene at 0.001-0.5% (w/v); diethylaminoethyl-dextran hydrochloride at 1-50 µg/ml; poly(D-glucosamine) at 0.005-2% (w/v); glucuronic acid-O-sulfatmucopolysaccharide at 50 to 500 U/ml; or poly-L-ornithine hydrobromide at 0.001-0.01% (w/v).

Furthermore, ionic strength in the suspension proliferation medium need to be adjusted with inorganic salts, preferably at the time of infection with an MOI below 1.0, for example, by supplementing with 1 volume of calcium chloride at 1.05 mM, cupric sulfate at 0.0000052 mM, ferric nitrate at 0.000124 mM, ferric sulfate at 0.0015 mM, magnesium chloride at 0.3 mM, magnesium sulfate at 0.407 mM, potassium chloride at 4.16 mM, sodium bicarbonate at 14.29 mM, sodium chloride at 120.61 mM, sodium bromide at 2.0 mM, sodium phosphate dibasic at 0.5 mM, sodium phosphate monobasic at 0.453 mM, and zinc sulfate at 0.432 mg/l.

Finally, the infection process is further supported by metabolic supplements and nutrients such as adding D-glucose with at least 3000 mg/l, hypoxanthine at 0.015 mM, linoleic acid at 0.042 mg/l, lipoic acid at 0.105 mg/l, putrescine HCl at 0.081 mg/l, sodium pyruvate at 55 mg/l, galactose with at least 300 mg/l and thymidine at 0.365 mg/l.

Each supplementation by itself has limited effect on MVA productivity in animal-derived component free media but in combination obtained yields approach and often exceed yields observed in cells infected and cultivated in FCS-supplemented basal medium. In FIG. 11 the above described steps are increased ionic strength to 25 mM NaCl in second panel or addition of serum as an example for a complex nutrient mix, metabolic supplementation in third panel, indicated polymethylene addition to 50 µg/ml in fourth panel and finally combination of all components in the last column of the fourth panel. The image of the monolayer in panel A also clearly demonstrates restored MVA replication in the thus supplemented medium.

Example 6

Human Adenovirus in *Rousettus* Cells

To determine whether *Rousettus* cells may be permissive for yet another virus not expected to proliferate in these cells of this species R06E and R05T lines were infected with E1-deleted adenovirus vector that expresses GFP (AdGFP). Infection was performed with an MOI of less than 0.1 to determine true spread of virus in the culture. As controls, HEK 293 cells (a human cell line known to be highly permissive for adenovirus) and duck CR cells (not permissive for adenovirus) were infected in parallel. Common to all cell lines examined here is expression of human adenovirus serotype 2 E1-region so that the E1-deleted vector is trans-complemented in all hosts.

Figure 12:
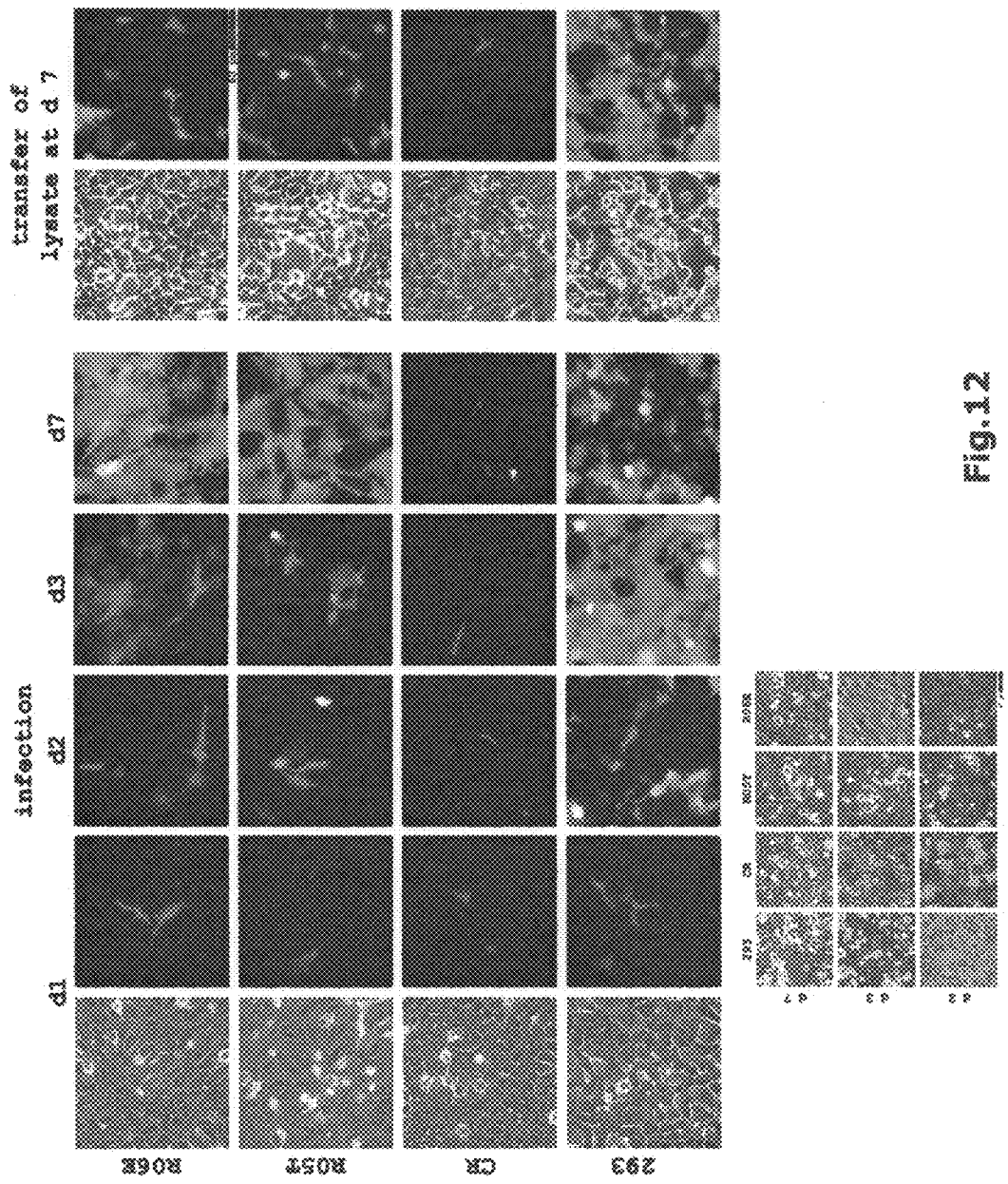

FIG. 12 clearly demonstrates that human adenovirus does spread in *rousettus* cells. Almost all cells of the *rousettus* culture exhibit GFP-expression within 7 days post infection. In the CR negative control there is no spread of GFP beyond occasional limited mitotic division of AdGFP-positive cells. In the HEK 293 culture the vector clearly spreads much faster and to superior levels compared to *rousettus* cells. A crude thaw/freeze lysate of infected HEK 293 cells transfers an expected high amount AdGFP to naive HEK 293 cells, a low amount of virus from *rousettus* cells, and extemely rarely input virus-derived vector from the CR cells. Thus, *rousettus* surprisingly is permissive for human adenovirus but apparently at lower levels of efficiency compared to HEK 293 cells.

Truly unexpected, however, is that AdGFP replication does not cause any cytopathic effect and that the GFP signal intensity declines until it is barely visible within 3 to 4 passages. Thus, virus after strong initial spread appears to be cleared from the culture.

In co-cultivation experiments AdGFP can be transfered to HEK 293 cells. For this experiment, R06E cells were infected with AdGFP and passaged at least three times to reliably remove any lingering input virus. After the third and fourth passage the infected R06E cells were mixed with an equal amount of HEK 293 cells, shown in FIG. 13. The two cell lines can be differentiated by size and morphology: HEK 293 are smaller than R06E, more compact with more distinctive phase contrast and better visible nuclei. Note the weak expression of GFP especially in the latently infected R06E after the fourth passage (images below day 0 in the lower panel). This experiment demonstrates that AdGFP is produced by the latently infected *rousettus* cells and can be transfered to co-cultivated HEK 293. AdGFP levels decline in the infected R06E monolayer and consequently efficiency of transfer decreases with sub-passage.

Figure 13:
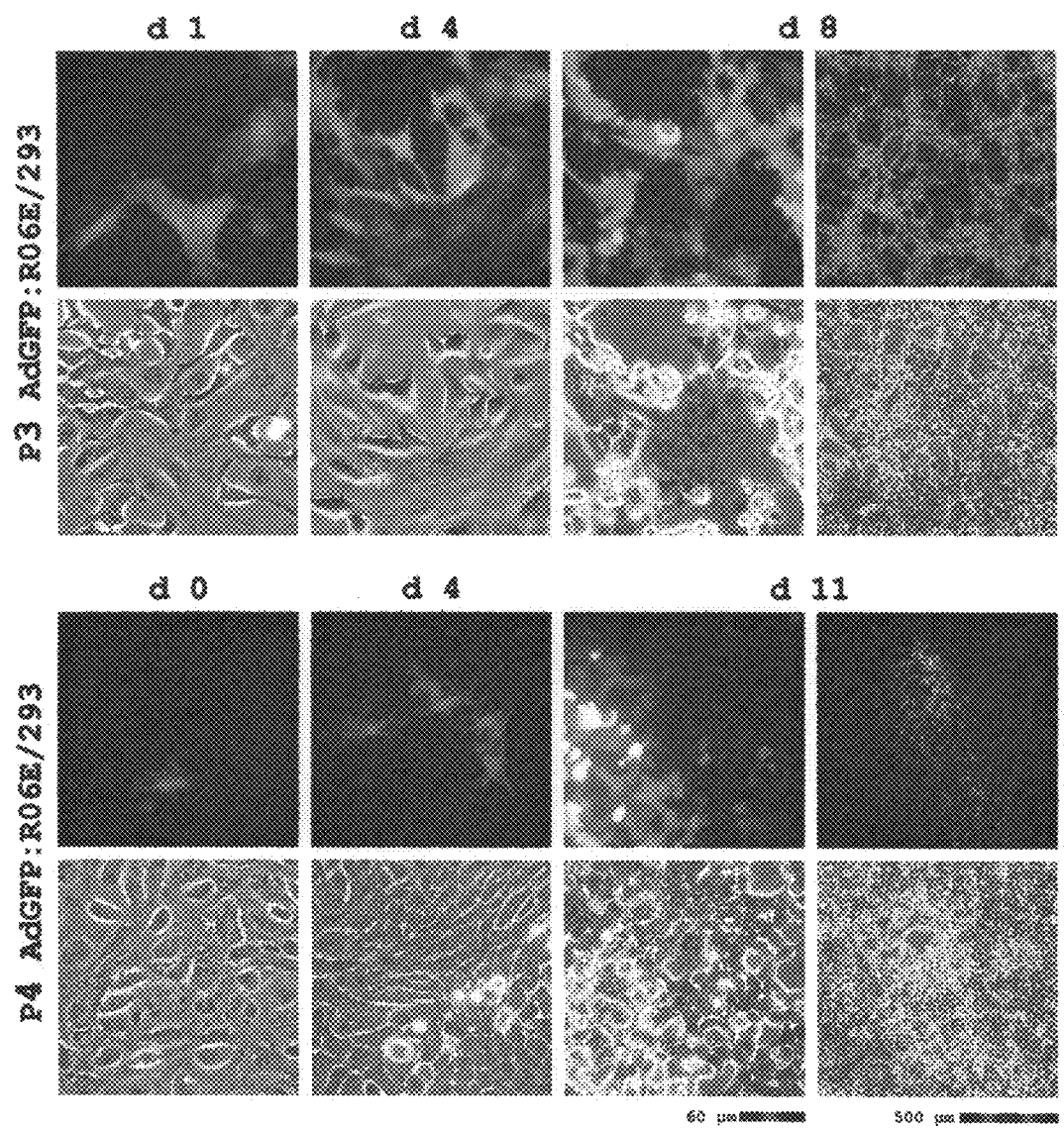

Highly interesting, co-cultivation also revealed that even at the tremendous MOIs expected when virus is released from neighboring HEK 293 the *rousettus* target cells maintained full proliferative potential, did not succumb to cytopathic effect and started to spread into the areas liberated by infected HEK 293 cells (note apparently healthy cells in the upper panel of FIG. 13 at day 8). GFP expression did increase in most *rousettus* cells but even there not to levels comparable even to refractory CR cells.

Figure 14:
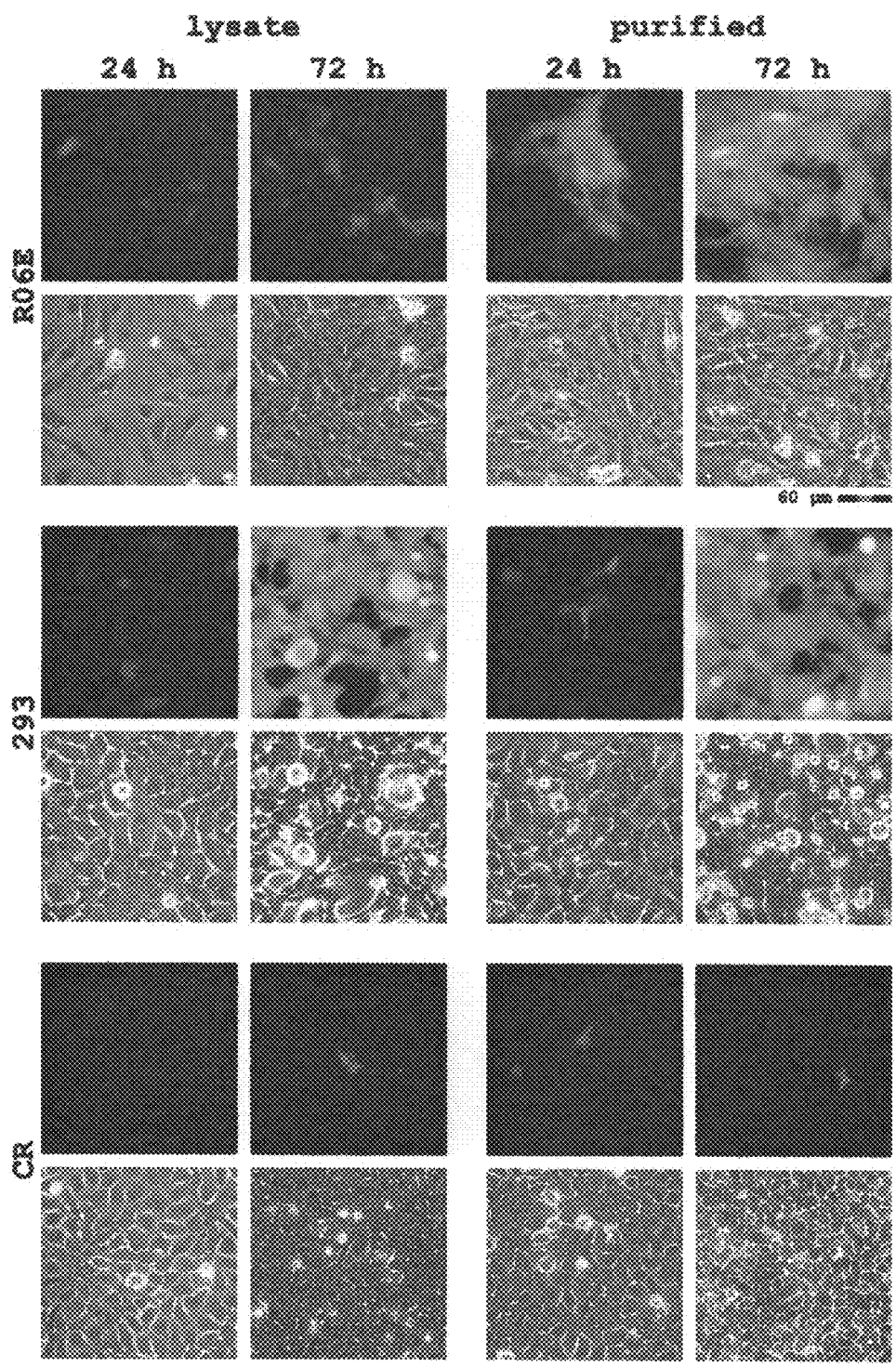

Truly astonishing and fully unexpected is the observation that susceptibility of R06E to AdGFP varies with the nature of the inoculum: AdGFP was given to cell monolayers either as crude thaw/freeze lysates from infected HEK 293 cells or purified by ultracentrifugation through a CsCl gradient (FIG. 14). Purification removes cellular debris from a freeze/thaw lysate by clarification at 5000×g; by incubation with 10 u/ml benzonase for 30 min; by banding with 105000×g in CsCl gradient consisting of layers of 1.5 g/cm$^3$, 1.35 g/cm$^3$ and 1.25 g/cm$^3$ in 10 mM TRIS HCl and 1 mM EDTA, pH 7.5; followed by a desalting step with a BioRad DG10 column. All preparations contain infectious AdGFP and for HEK 293 cells there are no differences in dynamic and intensity of spread of GFP signal. A crude lysate, however, may also contain a number of pathogen associated signals and cellular messengers already examined in Example 4. These signals and/or messengers do not impact on HEK 293 but have a clearly visible effect on *rousettus* cells. Not all lysates trigger this effect.

We speculate that in our screen for the susceptibility spectrum of *rousettus* cells we have unexpectedly found cell lines that are capable of launching an extremely efficient and truly protective antiviral response when challenged with certain pathogens (the system appears to fail with MVA but is very successful with AdV). Such a mechanism would also explain the observation that AdGFP infection is occult or masked without CPE and that after an initial multiplication virus is lost from the culture with repeated subculturing. In co-cultivation with highly susceptible HEK 293 virus is transmitted but re-infection and super-infection at very high MOIs appears to be limited as GFP signal intensity remains low in *rousettus* and proliferation (at least initially) is not disturbed.

Thus, using AdGFP as a tester virus (obviously, additional viruses will be identified) it is possible to screen for unique factors from these unusual mammals that mediate the protective effect, or to use these cells as highly sensitive detection system for common pathways. From such a screen it is possible (for example, by differential expression analysis and proteomic approaches) to identify the factors, the involved pathways, and small chemicals that may trigger or interfere with these responses. An isolated, unique factor may provide a novel therapeutic protein. A newly discovered anti-viral pathway may lead to new strategies for eliciting these responses in a human patient or diseased animal. Small chemicals may provide supportive therapeutic approaches for treatment of acute or chronic infectious and non-infectious (such as auto-immune) diseases.

Sequence Listing (Free Text)
SEQ ID NO:1 transfection vector #G56
SEQ ID NOs:2-7 primers

---

The invention claimed is:

1. An isolated immortalized bat cell line having stably integrated into its genome an E1 region from human adenovirus serotype 5, wherein the E1 region encodes E1A and E1B proteins, wherein the E1A and E1B proteins consist of E1A and E1B proteins encoded by nucleotides 3524 to 8361 of SEQ ID NO: 1, wherein said proteins are functionally expressed in said cell.

2. The cell line according to claim 1 which is a fruit bat cell line.

3. The cell line according to claim 1, which additionally carries at least one non-native functional sequence selected from the group consisting of transgenes, promoters, enhancers, selection markers, reporter genes, and therapeutic genes.

4. The cell line according to claim 1, which has at least one property selected from the group consisting of (i) if contacted with a microbial agent, replicates the microbial agent; and (ii) proliferates in medium free of animal-derived components.

5. The cell line according to claim 1, which is a *Rousettus aegyptiacus* cell line.

6. A method for preparing the cell line according to claim 1, which comprises immortalizing a starting bat cell with by stably integrating an E1 region from human adenovirus serotype 5 into the genome of said bat cell, wherein the E1 region encodes E1A and E1B proteins, wherein the E1A and E1B proteins consist of E1A and E1B proteins encoded by nucleotides 3524 to 8361 of SEQ ID NO: 1, wherein said proteins are functionally expressed in said cell.

7. The cell line of claim 2, wherein the bat cell is selected from the group consisting of a fetal cell, a neonatal cell, and a cell from neuronal tissue.

8. The cell line of claim 2, wherein the fruit bat is a *Rousettus aegyptiacus* species.

9. The cell line of claim 3, wherein the transgenes are genes complementing deficient viruses.

10. The cell line of claim 9, wherein the genes complementing deficient viruses are selected from the group consisting of a Epstein-Barr Nuclear Antigen 1 (EBNA1) transactivator and a viral structural protein.

11. The cell line of claim 3, comprising non-native promoters, wherein the promoters are selected from the group consisting of phosphoglycerate kinase- (PGK-), elongation factor-1 alpha- (EF1a-), cytomegalovirus-(CMV-), and thymidine kinase- (tk-) promoters.

12. The cell line of claim 3, wherein the enhancers are Rous sarcoma virus log terminal repeats (RSV-LTR).

13. The cell line of claim 3, wherein the selection markers are selected from the group consisting of neomycin-resistance and puromycin-resistance selection markers.

14. The cell line of claim 3, wherein the reporter genes are selected from the group consisting of green fluorescent protein (GFP) and beta-galactosidase (LacZ).

15. The cell line of claim 3, wherein the therapeutic genes are genes encoding antibodies.

16. The cell line of claim 4, wherein the microbial agent is selected from the group consisting of a virus and a viral vector.

17. The cell line of claim 1, wherein the cell line is the cell line AGE1.R06E deposited under DSM ACC2902.

* * * * *